United States Patent
Karaborni et al.

(10) Patent No.: US 11,357,734 B2
(45) Date of Patent: *Jun. 14, 2022

(54) PHARMACEUTICAL GRANULATIONS OF WATER-SOLUBLE ACTIVE PHARMACEUTICAL INGREDIENTS

(71) Applicant: XWPHARMA LTD., Grand Cayman (KY)

(72) Inventors: Sami Karaborni, Cupertino, CA (US); William W. Xiang, Fremont, CA (US); Daniel M. Canafax, Half Moon Bay, CA (US); Jia-Ning Xiang, Fremont, CA (US)

(73) Assignee: XWPHARMA LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/350,478

(22) Filed: Jun. 17, 2021

(65) Prior Publication Data

US 2021/0393537 A1    Dec. 23, 2021

Related U.S. Application Data

(60) Provisional application No. 63/040,780, filed on Jun. 18, 2020.

(51) Int. Cl.
*A61K 9/50* (2006.01)
*A61K 9/00* (2006.01)
*A61K 31/195* (2006.01)
*A61K 47/02* (2006.01)
*A61K 47/38* (2006.01)

(52) U.S. Cl.
CPC .......... *A61K 9/5073* (2013.01); *A61K 9/0053* (2013.01); *A61K 31/195* (2013.01); *A61K 47/02* (2013.01); *A61K 47/38* (2013.01)

(58) Field of Classification Search
None
See application file for complete search history.

(56) References Cited

U.S. PATENT DOCUMENTS

| | | |
|---|---|---|
| 4,370,338 A | 1/1983 | Mizoule |
| 5,110,797 A | 5/1992 | Ienaga et al. |
| 6,489,350 B1 | 12/2002 | Benedyk et al. |
| 7,482,429 B2 | 1/2009 | Albericio et al. |
| 7,521,455 B2 | 4/2009 | Nagase et al. |

(Continued)

FOREIGN PATENT DOCUMENTS

| | | |
|---|---|---|
| CN | 1422278 | 6/2003 |
| CN | 101511388 | 8/2009 |

(Continued)

OTHER PUBLICATIONS

Cameo Chemicals, ethyl-3-hydroxybutyrate [(retrieved from https://web.archive.org/web/20170209085248/https://cameochemicals.noaa.gov/chemical/20385)], 2017. (Year: 2017).*

(Continued)

*Primary Examiner* — Kyung S Chang

(57) ABSTRACT

Granulations with granules having a high loading of an active pharmaceutical ingredient are disclosed. The active pharmaceutical ingredient has a high aqueous water solubility. The granules have a narrow particle size distribution and a smooth exterior surface.

18 Claims, 28 Drawing Sheets

(56) References Cited

U.S. PATENT DOCUMENTS

| | | | |
|---|---|---|---|
| 7,960,561 | B2 | 6/2011 | Sorensen et al. |
| 8,529,954 | B2 | 9/2013 | Lebon et al. |
| 8,598,191 | B2 | 12/2013 | Liang et al. |
| 9,309,182 | B2 | 4/2016 | Tung et al. |
| 10,398,662 | B1 * | 9/2019 | Allphin ............ A61K 31/785 |
| 10,457,627 | B2 | 10/2019 | Xiang et al. |
| 10,501,401 | B2 | 12/2019 | Xiang et al. |
| 10,640,451 | B2 | 5/2020 | Xiang et al. |
| 10,774,031 | B2 | 9/2020 | Xiang et al. |
| 2004/0214755 | A1 | 10/2004 | Albericio et al. |
| 2005/0182045 | A1 | 8/2005 | Nagase et al. |
| 2006/0122383 | A1 | 6/2006 | Zhou et al. |
| 2006/0210630 | A1 | 9/2006 | Liang et al. |
| 2008/0175873 | A1 | 7/2008 | Zhou et al. |
| 2010/0144869 | A1 | 6/2010 | Nudelman et al. |
| 2011/0111027 | A1 * | 5/2011 | Rourke ............ A61K 9/2013 424/472 |
| 2011/0178068 | A1 | 7/2011 | Almarsson et al. |
| 2011/0293729 | A1 * | 12/2011 | Lebon ............ A61K 9/5026 424/494 |
| 2012/0283300 | A1 | 11/2012 | Kim et al. |
| 2016/0052862 | A1 | 2/2016 | Frost et al. |
| 2018/0193277 | A1 | 7/2018 | Suplie et al. |
| 2019/0183806 | A1 | 6/2019 | Guillard |
| 2020/0009076 | A1 | 1/2020 | Patel et al. |
| 2020/0223783 | A1 | 7/2020 | Xiang et al. |
| 2020/0276142 | A1 | 9/2020 | Grassot et al. |
| 2022/0023247 | A1 | 1/2022 | Xiang et al. |

FOREIGN PATENT DOCUMENTS

| | | |
|---|---|---|
| CN | 102076342 | 5/2011 |
| CN | 102834098 | 12/2012 |
| CN | 103370289 | 10/2013 |
| DE | 852392 | 10/1952 |
| EP | 0635265 | 1/1995 |
| EP | 2566462 | 3/2013 |
| FR | 2662695 | 12/1991 |
| JP | 62-270552 | 11/1987 |
| JP | 2002-503673 | 2/2002 |
| JP | 2003-522198 | 7/2003 |
| JP | 2004059452 | 2/2004 |
| JP | 2008-526713 | 7/2008 |
| JP | 2013-516465 | 5/2013 |
| RU | 2142800 | 12/1999 |
| WO | 1999/041275 | 8/1999 |
| WO | 1999/051613 | 10/1999 |
| WO | 2004/087169 | 10/2004 |
| WO | 2005/123731 | 12/2005 |
| WO | 2006/038226 | 4/2006 |
| WO | 2009/040331 | 4/2009 |
| WO | 2009/102462 | 8/2009 |
| WO | 2009/137717 | 11/2009 |
| WO | 2010/124046 | 10/2010 |
| WO | 2011/119839 | 9/2011 |
| WO | 2013/019561 | 2/2013 |
| WO | 2013/163244 | 10/2013 |
| WO | 2014/031840 | 2/2014 |
| WO | 2014/078014 | 5/2014 |
| WO | 2014/152263 | 9/2014 |
| WO | 2014/205393 | 12/2014 |
| WO | 2015/057884 | 4/2015 |
| WO | 2015/083129 | 6/2015 |
| WO | 2017/049470 | 3/2017 |
| WO | 2017/050259 | 3/2017 |
| WO | 2018/015563 A1 | 1/2018 |
| WO | 2018/098472 | 5/2018 |

OTHER PUBLICATIONS

International Search Report and Written Opinion for International Application No. PCT/CN2016/099763, dated Jan. 3, 2017, 15 pages.

International Search Report and Written Opinion for International Application No. PCT/CN2017/078873, dated Jan. 9, 2018, 12 pages.

International Search Report and Written Opinion for International Application No. PCT/CN2018/090151, dated Feb. 20, 2019, 14 pages.

International Search Report and Written Opinion for International Application No. PCT/CN2018/097241, dated Apr. 28, 2019, 11 pages.

International Search Report and Written Opinion for International Application No. PCT/CN2018/109115, dated Jul. 8, 2019, 11 pages.

International Search Report and Written Opinion for International Application No. PCT/CN2018/118565, dated Jul. 8, 2019, dated Apr. 28, 2019, 13 pages.

International Search Report and Written Opinion for PCT Application No. PCT/US2020/066047, dated Mar. 23, 2021, 11 pages.

Non-Final Office Action for U.S. Appl. No. 16/831,086, dated Apr. 13, 2020, 8 pages.

Non-Final Office Action for U.S. Appl. No. 16/791,243, dated Apr. 8, 2020, 20 pages.

Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.

Search Report for Australia Application No. 2017406159, dated Feb. 28, 2020, 6 pages.

Search Report for Australia Application No. 2016328150, dated Mar. 27, 2020, 4 pages.

Search Report for Russia Application No. 2019134607, dated Feb. 11, 2020, 7 pages (translation).

Jiang, et al., Copper-Catalyzed Aerobic Oxidative Regioselective Thiocyanation of Aromatics and Heteroaromatics. J. Org. Chem. 2017, 82, 18, 9312-9320.

Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.

Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.

Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.

Lee et al., "Development of an Immunoassay for the Residues of the Herbicide Bensulfuron-Methyl," Journal of Agricultural and Food Chemistry, Mar. 2002, vol. 50, No. 7, p. 1791-1803.

Luengo et al., "Synthesis and Structure-Activity Relationships of Macrocyclic FKBP Ligands", Bioorganic & Medicinal Chemistry Letters, 1994, vol. 4, No. 2, p. 321-324.

McGeer et al., "Pharmacologic Approaches to the Treatment of Amyotrophic Lateral Sclerosis", Drug Mechanisms and Targets, 2006, vol. 19, No. 1, p. 31-37.

RN 1243631-58-4, STN entry date Sep. 29, 2010.
STN Columbus, Registry Jul. 21, 1990, 128321-03-09, 81055-72-3.
STN Columbus, Registry Dec. 4, 2015, CAS No. 1822708-15-5.
RN 142229-71-8, STN entry date Jul. 3, 1992.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 1744-22-5, STN entry date Nov. 16, 1984.
RN 326-45-4, STN entry date Nov. 16, 1984.
RN 747353-64-6, STN REG, Sep. 17, 2004.
RN 60176-62-7, STN entry date Nov. 16, 1984.
RN 60176-63-8, STN REG, Nov. 16, 1984.
RN 60388-38-7, STN entry date Nov. 16, 1984.
CAS Registry No. 238401-16-6 entry date Sep. 10, 1999.

Rothweiler, et al., Probing the ATP-Binding Pocket of Protein Kinase DYRK1A with Benzothiazole Fragment Molecules. J. Med. Chem. 2016, 59, 21, 9814-9824.

(56) References Cited

OTHER PUBLICATIONS

Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.

Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.

Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.

Ward et al., "Discovery of an Orally Bioavailable Nki Receptor Antagonist, (2S, 3S)-(2-Methoxy-5-tetrazol-1-ylbenzyl)(2-phenylpiperidin-3-yl)amine (GR203040), with Potent Antiemetic Activity," Journal of Med. Chem., 1995, vol. 38, p. 4985-4992.

International Search Report and Written Opinion for PCT Application No. PCT/US2021/037830, dated Dec. 7, 2021, 20 pages.

International Search Report and Written Opinion for PCT Application No. PCT/US2021/037909, dated Dec. 2, 2021, 27 pages.

International Search Report and Written Opinion for PCT Application No. PCT/US2021/042818, dated Nov. 12, 2021, 13 pages.

Partial International Search Report and Written Opinion for PCT Application No. PCT/US2021/037830, dated Oct. 6, 2021, 14 pages.

Partial International Search Report and Written Opinion for PCT Application No. PCT/US2021/037909, dated Oct. 4, 2021, 26 pages.

During et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.

Cameo Chemicals, ethyl-3-hydroxybutyrate, retrieved from https://web.archive.org/web/20170209085248/ https://cameochemicals.noaa.gov/chemical/20385, 2017, 5 pages.

International Search Report and Written Opinion for PCT Application No. PCT/US2021/053640, dated Mar. 3, 2022, 18 pages.

* cited by examiner

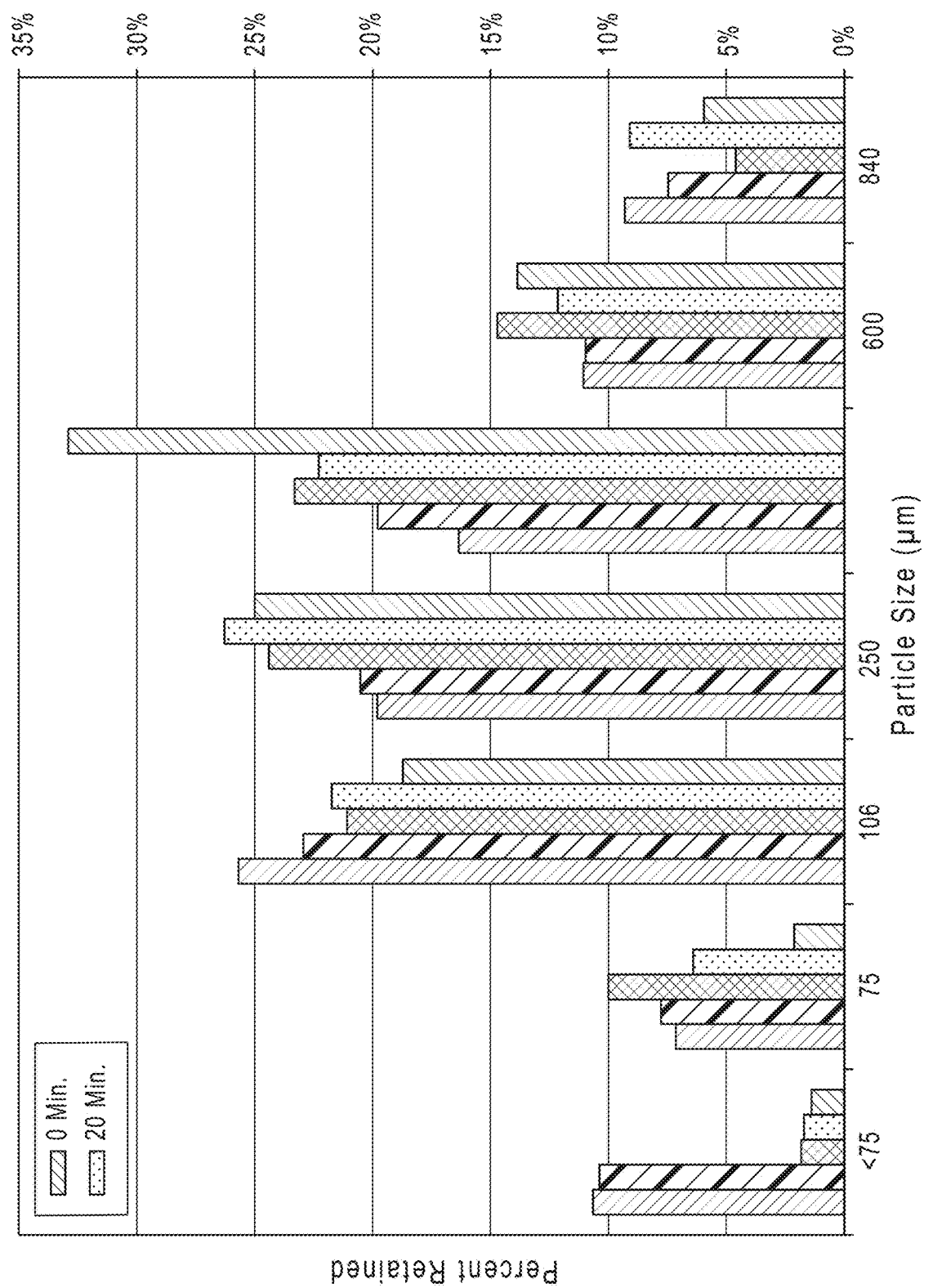

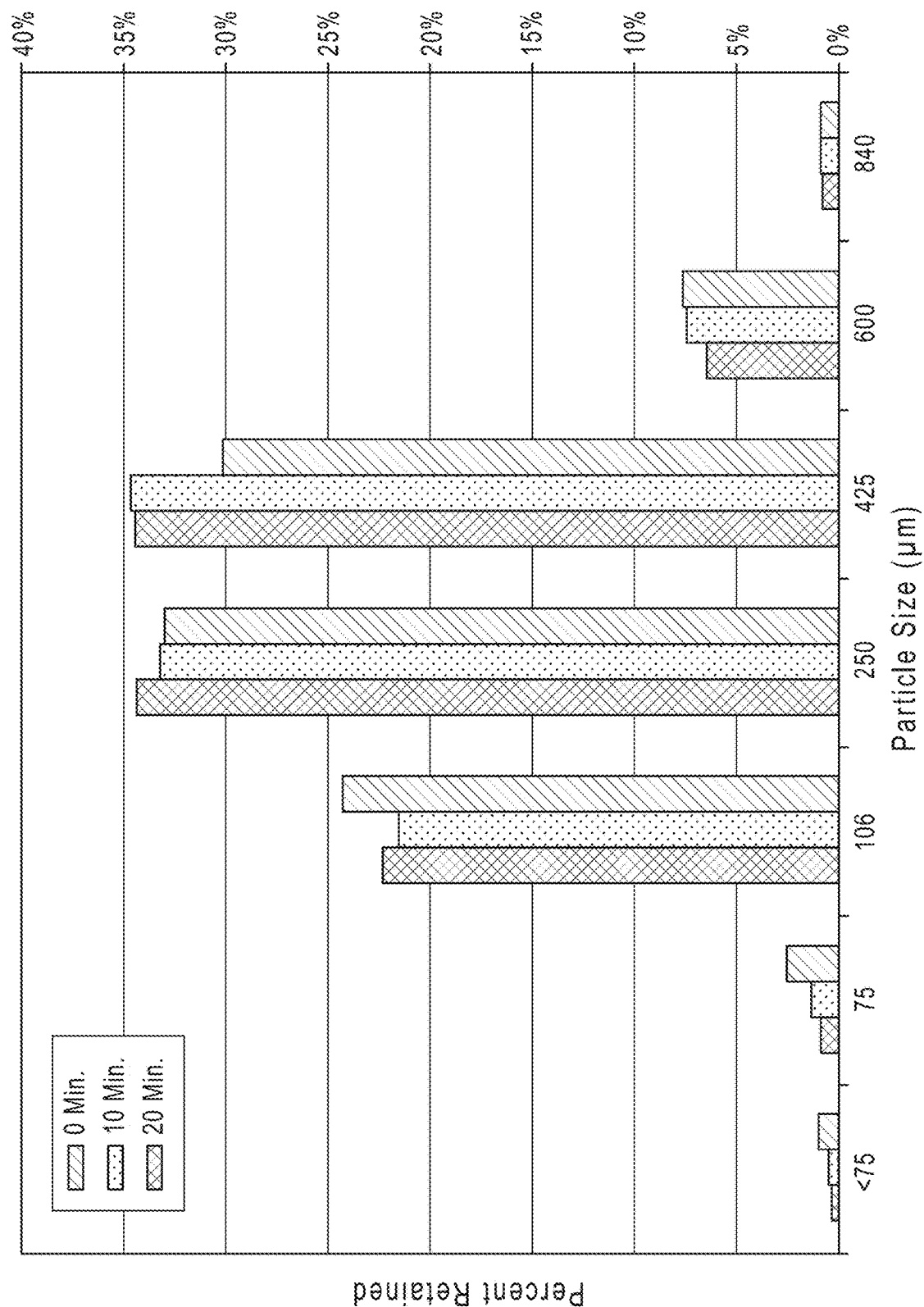

| Ex. | ¹First Granulation | | First Wet Massing | | | | ²Second Granulation | | Second Wet Massing | | | |
|---|---|---|---|---|---|---|---|---|---|---|---|---|
| | Water (wt%) | Time (min) | Time (min) | Temp (°C) | Mixer (rpm) | Chopper (rpm) | Water (wt%) | Time (min) | Time (min) | Temp (°C) | Mixer (rpm) | Chopper (rpm) |
| 1 | 3.76 | 7 | 30 | ³n/m | n/m | n/m | – | – | – | – | – | – |
| 2 | 3.69 | 6 | 46 | 30-36 | 800-1200 | 2000 | – | – | – | – | – | – |
| 3 | 8.75 | 30 | 36 | 17-33 | 850 | 3600 | – | – | – | – | – | – |
| 4 | 10 | 24 | 50 | 23-25 | 850 | 3600 | 4.5 | 12 | 30 | 25-29 | 850 | 3600 |
| 5 | 5.0 | 10 | 20 | 21-22 | 850 | 3600 | 6.6 | 26 | 40 | 25-31 | 850 547 | 3600 1800 |
| 6 | 5.0 | 10 | 20 | 21-22 | 547 | 1800 | 3.0 | 12 | 30 | 26-31 | 547 | 1800 |
| 7 | 5.0 | 10 | 20 | 23 | 547 | 1800 | – | – | – | – | – | – |
| 8 | 4.8 | 12 | 60 | 21-24 | 547 | 1800 | – | – | – | – | – | – |
| 9 | 4.7 | 10 | 60 | 23-24 | 547 | 1800 | – | – | – | – | – | – |

FIG. 11

| Property | Units | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| API | | $(2a)^1$ | $(2a)^1$ | $(2a)^1$ | $(2a)^1$ | $(2a)^1$ | $(2a)^1$ | $(2a)^2$ | $(2a)^2$ | $(2a)^3$ |
| API Bulk Density | g/mL | 0.5 | 0.5 | 0.5 | 0.5 | 0.5 | 0.5 | 0.341 | 0.341 | 0.263 |
| Granule Bulk Density | g/mL | .5 | – | 0.640 | 0.652 | 0.636 | 0.600 | 0.680 | 0.691 | 0.714 |
| PSD (D10) | μm | – | – | – | – | – | – | – | – | 106 |
| PSD (D50) | μm | – | – | – | – | – | – | – | – | 267 |
| PSD (D90) | μm | – | – | – | – | – | – | – | – | 533 |
| Yield (100-425 μm) | %w/w | 6 | 35 | 60 | 46 | 30 | 52 | 57 | 56 | 63 |
| Yield (200-350 μm) | %w/w | – | – | – | 31 | 16 | 29 | 31 | 38 | 36 |
| LOD | % | – | – | 0.6 | 7.38 | $6.62^3$ $6.21^4$ | 0.61 | 0.72 | 1.46 | 0.95 |
| Sphericity | 0<x<1.00 | – | – | – | – | – | – | – | – | – |
| Friability | % < 75 μm | – | – | – | – | – | – | – | – | 1.02 |

FIG. 12

PHARMACEUTICAL GRANULATIONS OF WATER-SOLUBLE ACTIVE PHARMACEUTICAL INGREDIENTS

This application claims the benefit under 35 U.S.C. § 119(e) of U.S. Provisional Application No. 63/040,780, filed on Jun. 18, 2020, which is incorporated by reference in its entirety.

FIELD

The invention relates to pharmaceutical granulations with granules having a high loading of an active pharmaceutical ingredient characterized by a high aqueous solubility. The granules have a narrow particle size distribution and a smooth exterior surface.

BACKGROUND

In certain methods of treatment, it is necessary to administer a high dose of an active pharmaceutical ingredient. To minimize the amount of the pharmaceutical formulation administered to a patient in such treatments, it is desirable that the pharmaceutical composition contain a high content of the active pharmaceutical ingredient and that the amount of pharmaceutical excipients be minimized.

Oral controlled-release dosage forms can contain granules coated with a coating that provides a desired release profile in the gastrointestinal tract. To facilitate achieving a desired oral controlled-release profile the oral dosage form can comprise a granulation comprising granules having a controlled-release coating.

To enhance the palatability of oral pharmaceutical suspensions it is desirable that the size of the particles containing the active pharmaceutical ingredient be less than 500 μm.

Pharmaceutical granulations having a high bulk density of an active pharmaceutical ingredient (API), a particle size less than 500 μm, and having surfaces amenable for coating are desired.

SUMMARY

According to the present invention, granulations comprise a plurality of granules, wherein, the granules comprise greater than 95 wt % of an active pharmaceutical ingredient (API), wherein wt % is based on the total weight of the granulation; and the active pharmaceutical ingredient comprises an aqueous solubility greater than 100 mg/mL.

According to the present invention, pharmaceutical compositions comprise a granulation according to the present invention.

According to the present invention, methods of preparing the granulation of according to the present invention comprise: combining the active pharmaceutical ingredient, a binder, and an antistatic agent to form a dry mixture; wet granulating the dry mixture to provide a wet granulation; wet massing the wet granulation to provide a wet massed granulation; and drying the wet massed granulation to provide the granulation.

BRIEF DESCRIPTION OF THE DRAWINGS

Those skilled in the art will understand that the drawings described herein are for illustration purposes only. The drawings are not intended to limit the scope of the present disclosure.

FIG. 4A shows the particle size distribution for pharmaceutical granulation (4) prepared using different wet massing times.

FIG. 7A shows the particle size distribution for pharmaceutical granulation (7) prepared using different wet massing times.

FIGS. 9A-9E show SEM images of pharmaceutical granulation (9) at two different magnifications.

FIG. 11 is a table summarizing granulation and wet massing processing conditions for Examples 1-9.

FIG. 12 is a table summarizing the properties for the granulations of Examples 1-9.

DETAILED DESCRIPTION

Figure 1A:
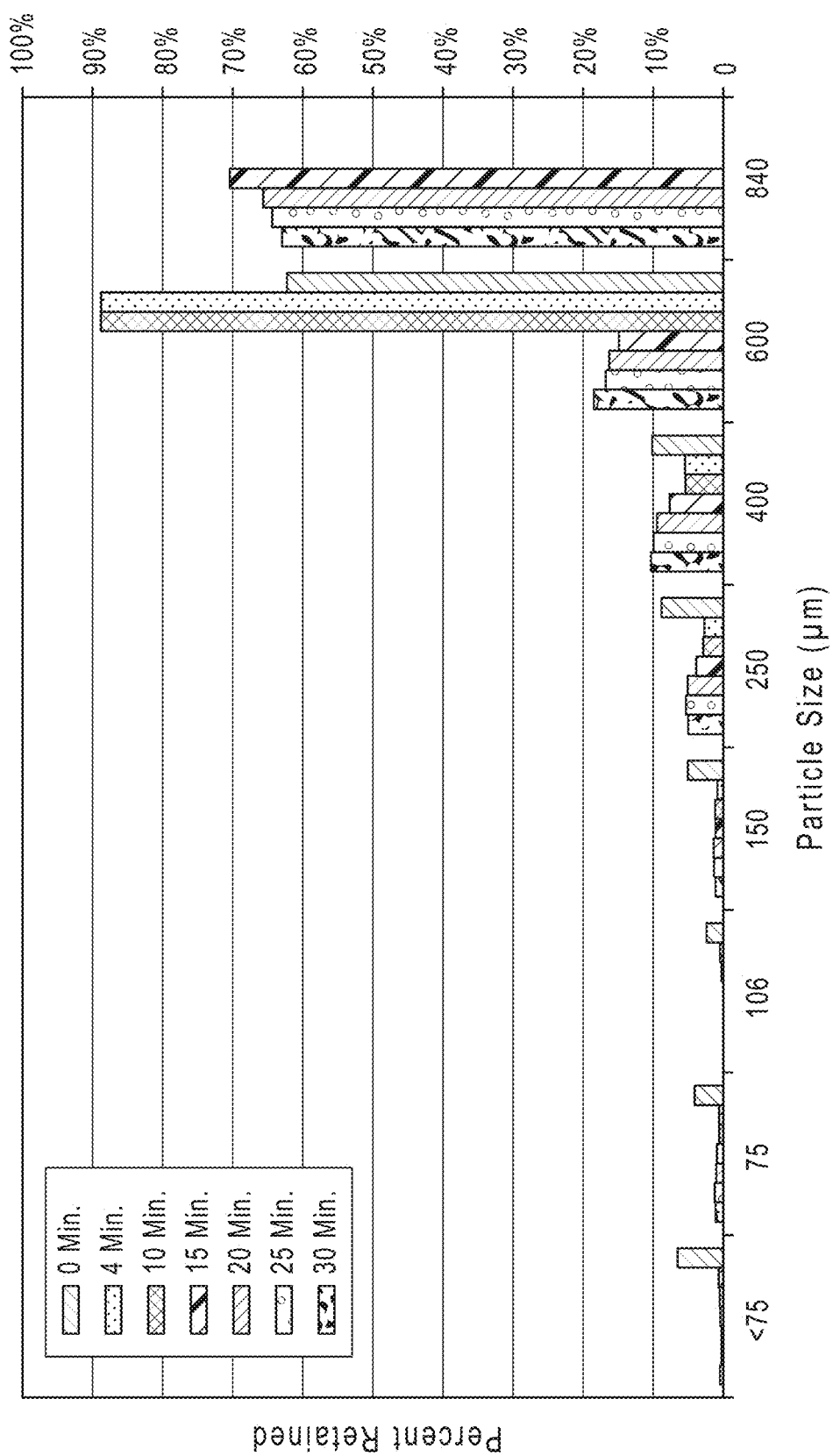
FIG. 1A shows the particle size distribution for pharmaceutical granulation (1) prepared using different wet massing times.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Immediate release" refers to a pharmaceutical composition that releases substantially all of an active pharmaceutical ingredient into the gastrointestinal tract of a patient within less than 1 hour following oral administration, such as less than 50 minutes, less than 40 minutes, less than 30 minutes, less than 20 minutes, or less than 10 minutes following oral administration. For example, an immediate release dosage from can release greater than 90%, greater than 95%, or greater than 98% of the active pharmaceutical ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate for active pharmaceutical ingredient that is absorbed into the systemic circulation from the upper portion of the gastrointestinal tract.

"Controlled release" pharmaceutical compositions include modified release formulations, delayed release formulations, extended release, and sustained release formulation. These formulations are intended to release an active pharmaceutical ingredient from the pharmaceutical composition at a desired rate and/or at a desired time following oral administration by a patient and/or at a certain location or locations with the gastrointestinal tract. The United States Pharmacopeia defines a modified release system as one in which the time course or location of drug release or both are chosen to accomplish objectives of therapeutic effectiveness or convenience not fulfilled by immediate release dosage forms. More specifically, modified release (MR) solid oral dosage forms include extended release (ER) and delayed release (DR) products. A delayed-release product is one that releases a drug all at once at a time other than promptly after administration. A modified release formulation can include delayed-release formulations using enteric coatings, site-specific or timed release formulations such as for colonic delivery, extended-release including, for example, formulations capable of providing zero-order, first-order, or biphasic release profiles, and programmed release such as pulsatile and delayed extended release.

"Alkoxy" refers to a radical —OR where R is alkyl. Examples of alkoxy groups include methoxy, ethoxy, propoxy, and butoxy. An alkoxy group can be, for example, $C_{1-6}$ alkoxy, $C_{1-5}$ alkoxy, $C_{1-4}$ alkoxy, $C_{1-3}$ alkoxy, ethoxy or methoxy.

"Alkyl" refers to a saturated, branched, or straight-chain, monovalent hydrocarbon radical derived by the removal of one hydrogen atom from a single carbon atom of a parent alkane. An alkyl group can be, for example, $C_{1-6}$ alkyl, $C_{1-5}$ alkyl, $C_{1-4}$ alkyl, or $C_{1-3}$ alkyl. An alkyl group can be methyl, ethyl, n-propyl, iso-propyl, or tert-butyl.

"Cycloalkyl" refers to a saturated cyclic alkyl radical. A cycloalkyl group can be, for example, $C_{3-6}$ cycloalkyl, $C_{3-5}$ cycloalkyl, $C_{5-6}$ cycloalkyl, cyclopropyl, cyclopentyl, or cyclohexyl. For example, a cycloalkyl can be selected from cyclopropyl, cyclobutyl, cyclopentyl, and cyclohexyl.

"Alkoxycarbonyl" refers to a radical —C(=O)—O—R where R can be $C_{1-6}$ alkyl such as $C_{1-4}$ alkyl, or $C_{1-3}$ alkyl. For example, R can be selected from methyl, ethyl, n-propyl, iso-propyl, and tert-butyl.

"Cycloalkoxycarbonyl" refers to a radical —C(=O)—O—R where R can be $C_{3-8}$ cycloalkyl, such as $C_{4-7}$ cycloalkyl or $C_{4-6}$ cycloalkyl. For example, R can be selected from cyclopropyl, cyclobutyl, cyclopentyl, and cyclohexyl.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof, or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

Bulk density can be determined according to USP 616, Method 1.

Tapped bulk density can be determined according to USP 616.

Specific surface area can be determined by laser diffraction.

The Hausner Ratio can be determined according to USP 1174.

The parameter D90 refers to the point in the size distribution of a sample, up to and including which, 90% of the total volume of material in the sample is contained. For example for a D90 of 400 µm, 90% of the sample volume has a size of 400 µm or less. D50 is the size below which 50% of the total volume of material in the sample is contained. Similarly, D10 refers to the size below which 10% of the total volume of material in the sample is contained. The volume distribution of the sample can be determined by laser diffraction or by sieve analysis.

Reference is now made to pharmaceutical granulations, compositions comprising the pharmaceutical granulation, and methods of making the pharmaceutical granulations. The disclosed pharmaceutical granulations, compositions comprising the pharmaceutical granulation, and methods of making the pharmaceutical granulations are not intended to be limiting of the claims. To the contrary, the claims are intended to cover all alternatives, modifications, and equivalents.

A granulation provided by the present disclosure comprises a plurality of granules, wherein the granules comprise greater than 95 wt %, such as greater than 98 wt %, or greater than 99 wt % of an active pharmaceutical ingredient, where wt % is based on the total weight of the granules; and the granulation is characterized by a particle size distribution (D50, the median diameter), for example, from 150 µm to 400 µm, from 150 µm to 350 µm, or from 150 to 300 µm. A granulation can be characterized by a D50, for example, of less than 450 µm, less than 400 µm, less than 350 µm, less than 300 µm less than 250 µm, or less than 200 µm.

A granule can comprise a high loading of an active pharmaceutical ingredient or a high loading of a combination of active pharmaceutical ingredients. For example, a granule can comprise greater than 95 wt %, greater than 96 wt %, greater than 97 wt %, greater than 98 wt %, or greater than 99 wt % of an active pharmaceutical ingredient, where wt % is based on the total weight of the granule. A granule can comprise, for example, from 95 wt % to 99.5 wt % of an active pharmaceutical ingredient, from 96 wt % to 99.5 wt % of an active pharmaceutical ingredient, from 96 wt % to 99 wt %, from 97 wt % to 99 wt %, or from 98 wt % to 99 wt % of an active pharmaceutical ingredient, where wt % is based on the total weight of the granule.

A granule can comprise an active pharmaceutical ingredient having a high aqueous solubility.

For example, an active pharmaceutical ingredient can have an aqueous solubility greater than 100 mg/mL, greater than 150 mg/mL, greater than 200 mg/mL, greater than 250 mg/mL, greater than 300 mg/mL, greater than 350 mg/mL, greater than 400 mg/mL, greater than 500 mg/mL, greater than 600 mg/mL. An active pharmaceutical ingredient can have an aqueous solubility, for example, from 100 mg/mL to 600 mg/mL, from 200 mg/mL to 500 mg/mL, or from 250 mg/mL to 450 mg/mL.

Aqueous solubility is determined by high pressure liquid chromatography (HPLC).

Examples of active pharmaceutical ingredient having a water solubility greater than 100 mg/mL include acetohydroxamic acid, aliskiren, amifostine, aminocaproic acid, aminolevulinic acid, aminophylline, ascorbic acid, benzethonium, benzphetamine, betazole, bretylium, bromotheophylline, brompheniramine, bronopol, bupropion hydrochloride, folinic acid, captopril, carbamoylcholine, chloral hydrate, cidofovir, citrulline, clavulanic acid, clindamycin, codeine phosphate, cycloserine, cysteamine, cytarabine, d-glucose, dinoprost tromethamine, d-serine, dyphylline, edetic acid, emtricitabine, esketamine hydrochloride, arketamine hydrochloride, ethambutol hydrochloride, ferrous bisglycinate, flurazepam, fomepizole, framycetin, gabapentin, gamma-aminobutyric acid, gemifloxacin, gentamicin, gluconic acid, gluconolactone, glucosamine, glutathione, ibandronate, ibutilide, isoniazid, ketorolac, lactitol, lactose, lactulose, levamisole hydrochloride, levetiracetam, levocarnitine, lisdexamfetamine, mannitol, metformin hydrochloride, methenamine, methimazole, methyl aminolevulinate, migalastat hydrochloride, miglustat, nalmefene hydrochloride, naltrexone hydrochloride, neostigmine bromide, netilmicin, nicotinamide, nicotine, nitrofural, norfloxacin, ornithine, oxycodone, penicillamine, pentoxyverine, phenformin, phenylephrine, phenylpropanolamine, pidolic acid, piperazine, piracetam, pregabalin, procarbazine hydrochloride, promethazine hydrochloride, pyridoxine, pyruvic acid, ranitidine hydrochloride, rolitetracycline, ropinirole, scopolamine, selenomethionine, sodium ascorbate, sodium oxybate, terbutaline, thiamine hydrochloride, tobramycin, tranexamic acid, tromethamine salt, valacyclovir, and venlafaxine hydrochloride, or a pharmaceutically acceptable salt of any of the foregoing.

An active pharmaceutical ingredient having a water solubility greater than 100 mg/mL include salt forms, hydrates, and/or solvates having a water solubility greater than 100 mg/mL where the parent active pharmaceutical ingredient has a water solubility less than 100 mg/mL.

An active pharmaceutical ingredient can comprise γ-hydroxy butyric acid or a derivative of γ-hydroxybutyric acid. γ-Hydroxybutyric acid has the structure of Formula (1):

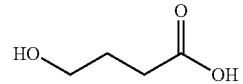

(1)

A prodrug derivative of γ-hydroxybutyric acid can have the structure of Formula (2):

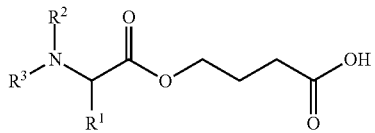

(2)

or a pharmaceutically acceptable salt thereof, wherein,
$R^1$ can be selected from hydrogen and $C_{1-6}$ alkyl; and
each of $R^2$ and $R^3$ can independently be selected from hydrogen, $C_{1-6}$ alkyl, $C_{1-6}$ alkoxycarbonyl, and $C_{3-8}$ cycloalkoxycarbonyl.

In compounds of Formula (2), $R^1$ can be selected from hydrogen and $C_{1-3}$ alkyl.

In compounds of Formula (2), $R^1$ can be selected from hydrogen, methyl, ethyl, n-propyl, and iso-propyl.

In compounds of Formula (2), $R^1$ can be iso-propyl.

In compounds of Formula (2), at least one of $R^2$ and $R^3$ can be selected from hydrogen and $C_{1-3}$ alkyl.

In compounds of Formula (2), each of $R^2$ and $R^3$ can independently be selected from hydrogen and $C_{1-3}$ alkyl.

In compounds of Formula (2), each of $R^2$ and $R^3$ can be hydrogen.

In compounds of Formula (2), $R^1$ can be selected from hydrogen and $C_{1-3}$ alkyl; and $R^2$ can be selected from $C_{1-6}$ alkoxycarbonyl and $C_{5-6}$ cycloalkoxycarbonyl.

In compounds of Formula (2), each of $R^2$ and $R^3$ can be hydrogen; and $R^1$ can be selected from hydrogen and $C_{1-3}$ alkyl.

In compounds of Formula (2), each of R and $R^3$ can be hydrogen; and $R^1$ can be selected from methyl, ethyl, n-propyl, and iso-propyl.

In compounds of Formula (2), each of $R^2$ and $R^3$ can be hydrogen; and $R^1$ can be iso-propyl.

In compounds of Formula (2), the carbon atom to which $R^1$ is bonded can be in the (R)-configuration.

In compounds of Formula (2), the carbon atom to which $R^1$ is bonded can be in the (S)-configuration.

A compound of Formula (2) can be selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

A compound of Formula (2) can be 4-((L-valyl)oxy) butanoic acid (2a) or a pharmaceutically acceptable salt thereof:

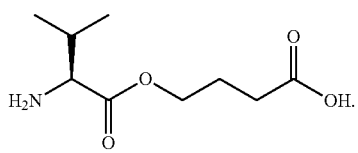

(2a)

A compound of Formula (2) can be 4-(glycyloxy)butanoic acid (2b) or a pharmaceutically acceptable salt thereof:

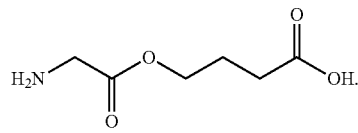

(2b)

A compound of Formula (2) can be 4-((L-alanyl)oxy) butanoic acid (2c) or a pharmaceutically acceptable salt thereof:

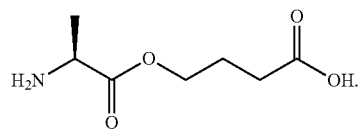

(2c)

Compounds of Formula (2)-(2c) are prodrugs of γ-hydroxybutyric acid, which when orally administered. provide γ-hydroxybutyric acid in the blood of a patient. Compounds of Formula (2)-(2c) exhibit a relative oral bioavailability of γ-hydroxybutyric acid in a patient of greater than 10% F, greater than 20% F, greater than 30% F, greater than 40% F, greater than 50% F, or greater than 60% F Before incorporating into granules, an active pharmaceutical ingredient can have a high bulk density.

An active pharmaceutical ingredient can have a bulk density, for example, less than 0.20 g/mL, less than 0.30 g/mL, less than 0.40 g/mL, or less than 0.50 g/mL.

An active pharmaceutical ingredient can have a bulk density, for example, from 0.15 g/mL to 0.33 g/mL, from 0.16 g/mL to 0.32 g/mL, from 0.17 g/mL to 0.31 g/mL, from 0.18 g/mL to 0.30 g/mL, from 0.19 g/mL to 0.29 g/mL, or from 0.20 g/mL to 0.28 g/mL.

An active pharmaceutical ingredient can have a tapped bulk density, for example, from 0.15 g/mL to 0.50 g/mL, from 0.20 g/mL to 0.45 g/mL, from 0.25 g/mL to 0.40 g/mL, or from 0.30 g/mL to 0.40 g/mL.

An active pharmaceutical ingredient can have a particle size distribution characterized, for example, by a D10 from 1 μm to 3 μm, a D50 from 6.5 μm to 8.5 μm, and a D90 from 15 μm to 17 μm.

Figure 9A:
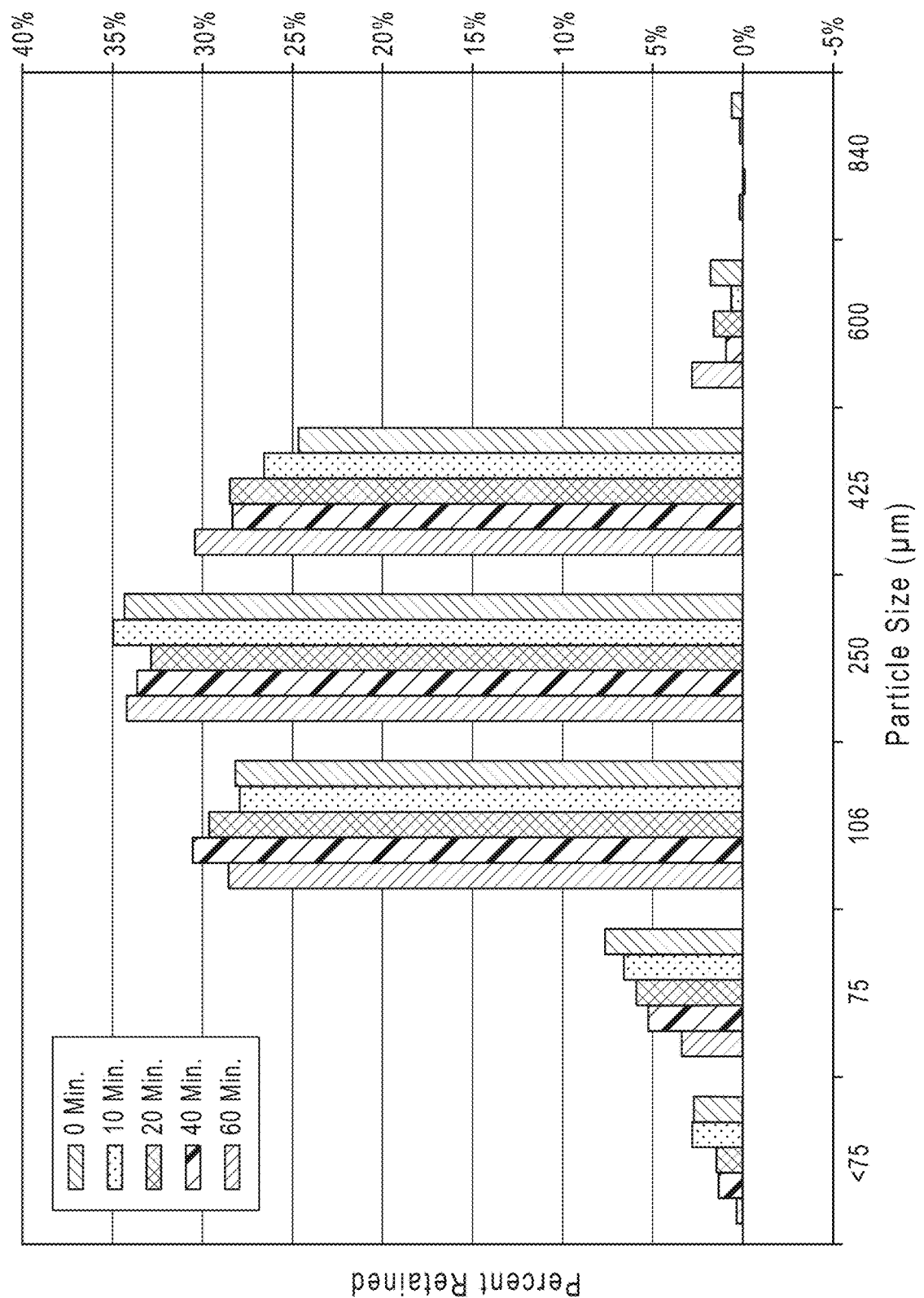
FIG. 9A shows the particle size distribution for pharmaceutical granulation (9) prepared using different wet massing times.
Figure 9B:
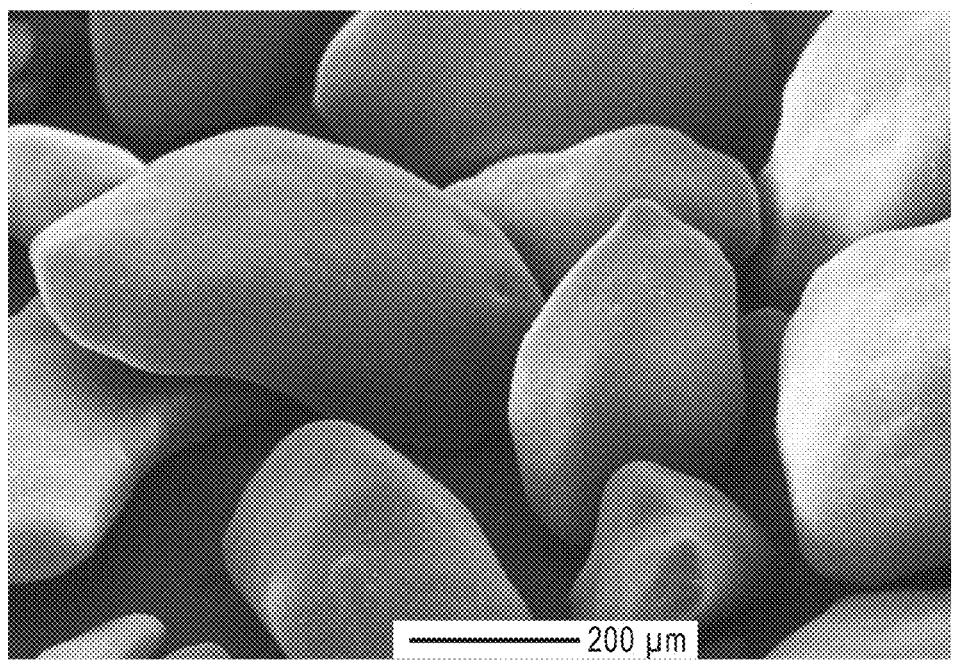
Figure 9C:
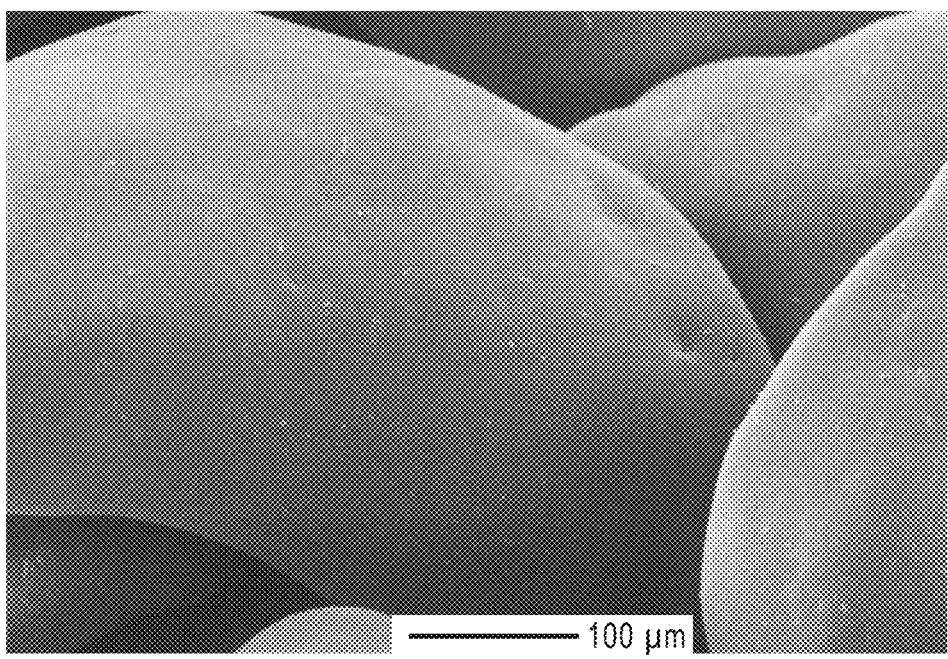
Figure 9D:
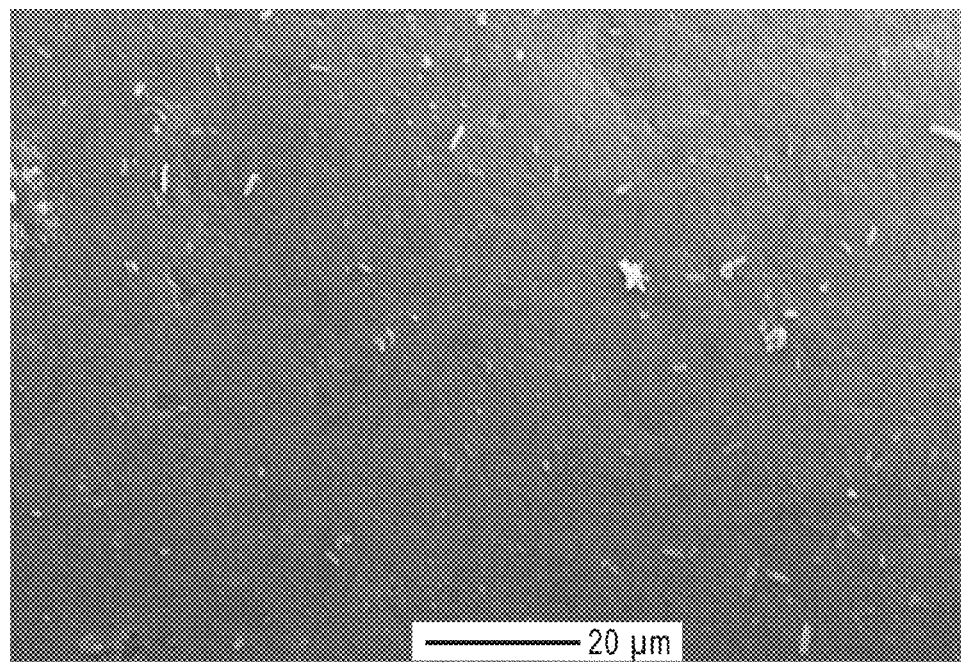
Figure 9E:
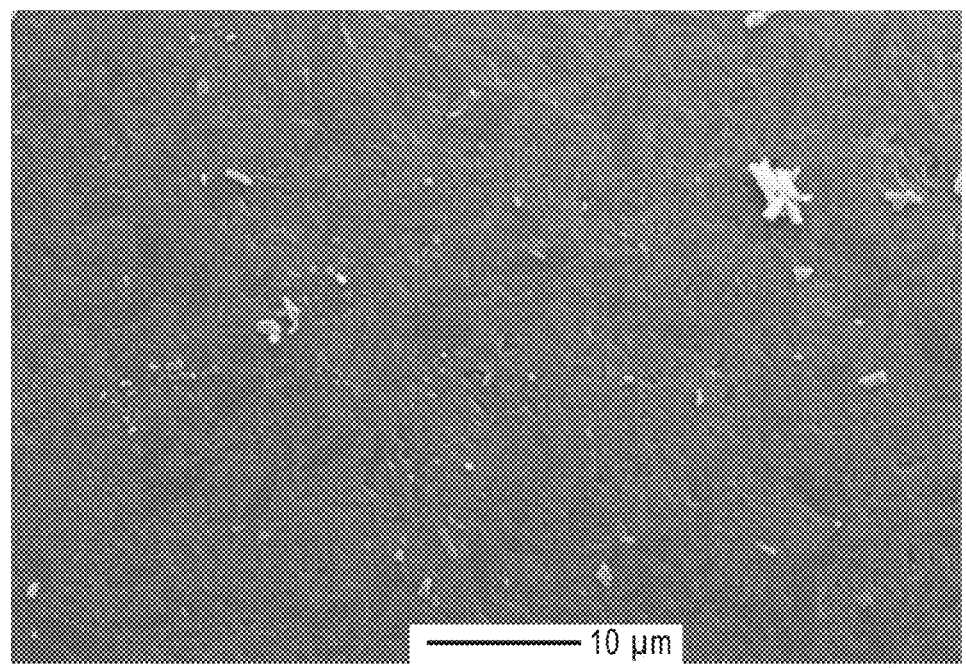
Figure 9F:
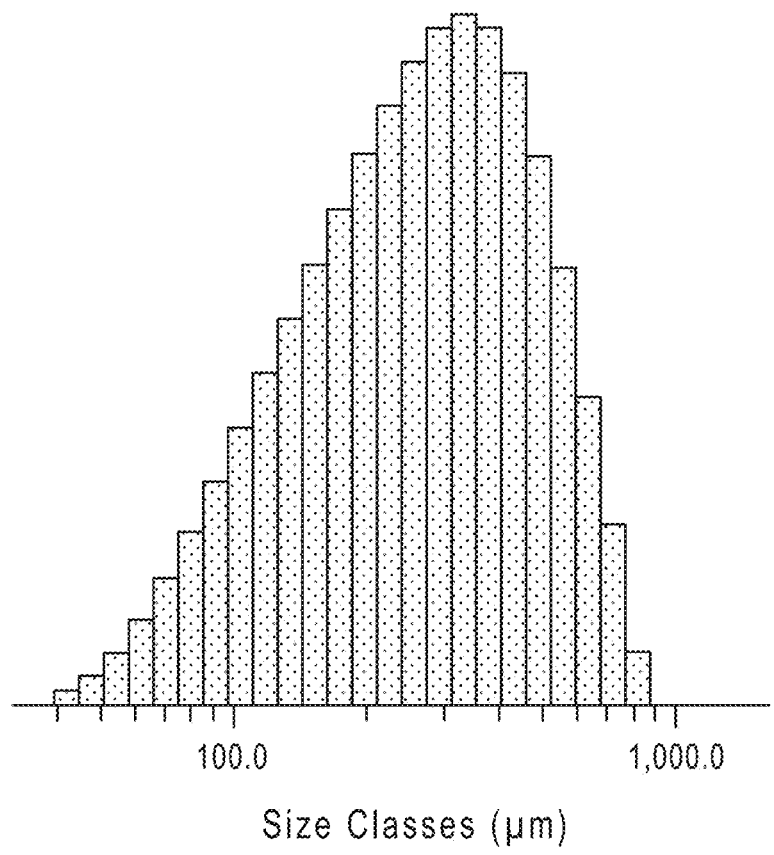
FIG. 9F shows the size distribution of the particles used to form pharmaceutical granulation (9).

An active pharmaceutical ingredient can have a particle size distribution, for example, as substantially shown in FIG. 9F.

An active pharmaceutical ingredient can be jet milled to reduce the particle size.

An active pharmaceutical ingredient can have a bulk density, for example, from 0.10 g/mL to 0.30 g/mL, from 0.12 g/mL to 0.28 g/mL, from 0.14 g/mL to 0.26 g/mL, from 0.16 g/mL to 0.24 g/mL, or from 0.18 g/mL to 0.22 g/mL.

An active pharmaceutical ingredient can have a tapped bulk density, for example, from 0.15 g/mL to 1 g/mL, from 0.15 g/mL to 0.8 g/mL, from 0.15 g/mL to 6 g/mL, from 0.25 g/mL to 0.50 g/mL, from 0.27 g/mL to 0.48 g/mL, from 0.29 g/mL to 0.46 g/mL, from 0.31 g/mL to 0.44 g/mL, or from 0.33 g/mL to 0.42 g/mL.

An active pharmaceutical ingredient can have a specific surface area, for example, from 200 m²/kg to 1200 m²/kg, such as from 400 m²/kg to 1000 m²/kg, or from 400 m²/kg to 800 m²/kg, wherein the specific surface area is determined using laser diffraction. An active pharmaceutical ingredient can have a specific surface area, for example, greater than 200 m$^2$/kg, greater than 400 m$^2$/kg, greater than 600 m$^2$/kg, greater than 800 m$^2$/kg, greater or greater than 1,000 m$^2$/kg.

An active pharmaceutical ingredient can have a particle size distribution characterized, for example, by a D10 from 10 μm to 14 μm, a D50 from 32 μm to 36 μm, and a D90 from 65 μm to 80 μm.

Figure 16:
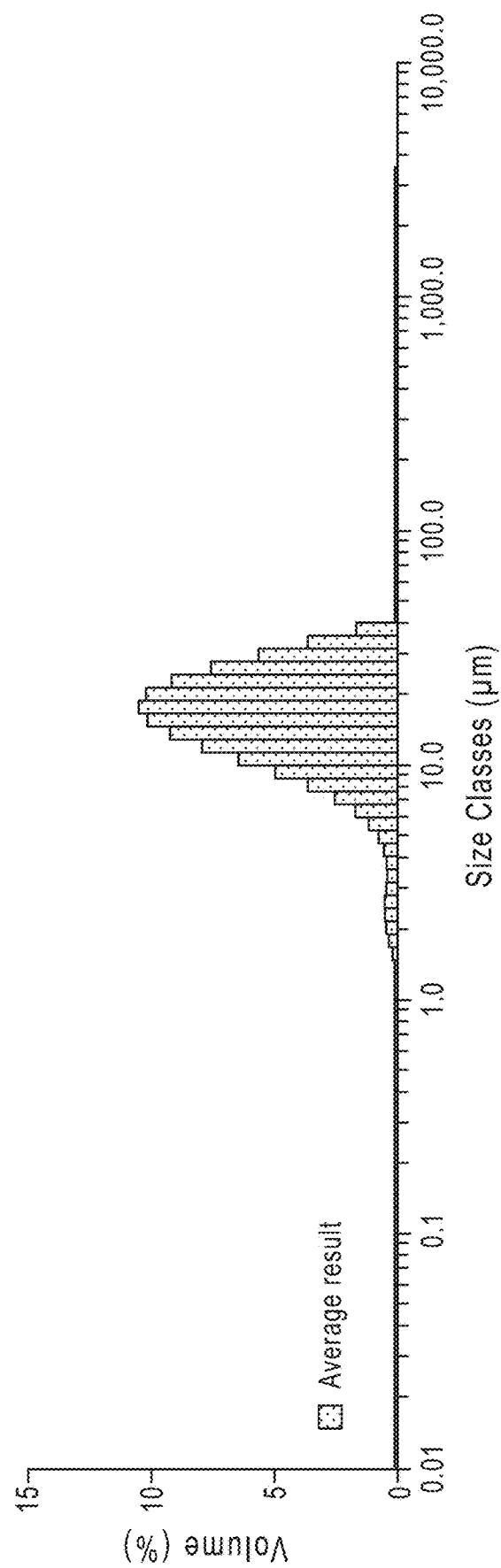
FIG. 16 shows the particle size distribution of the active pharmaceutical ingredient described in Example 13 after jet-milling.
Figure 17:
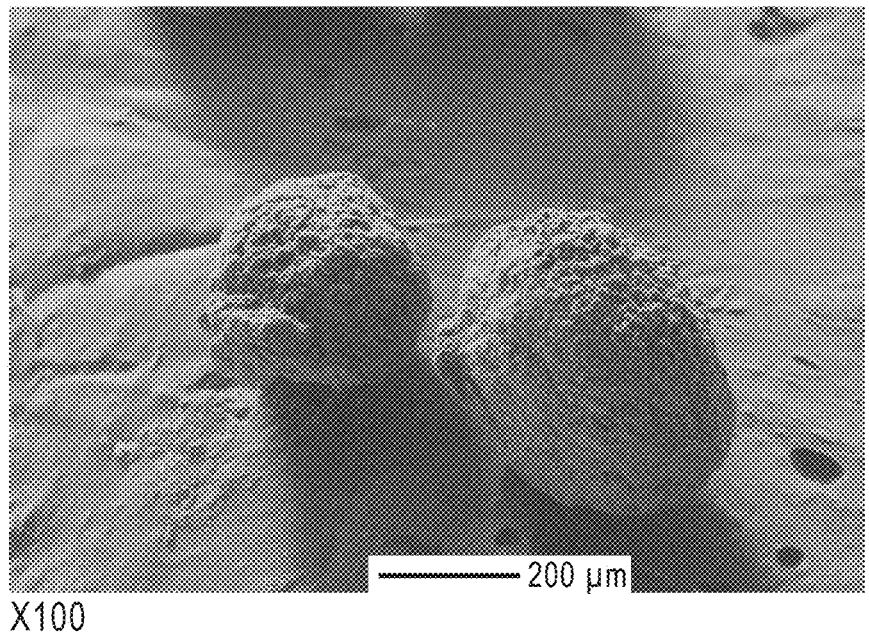
FIG. 17 shows an SEM image of granules prepared as described in Example 13 at 100× magnification.
Figure 18:
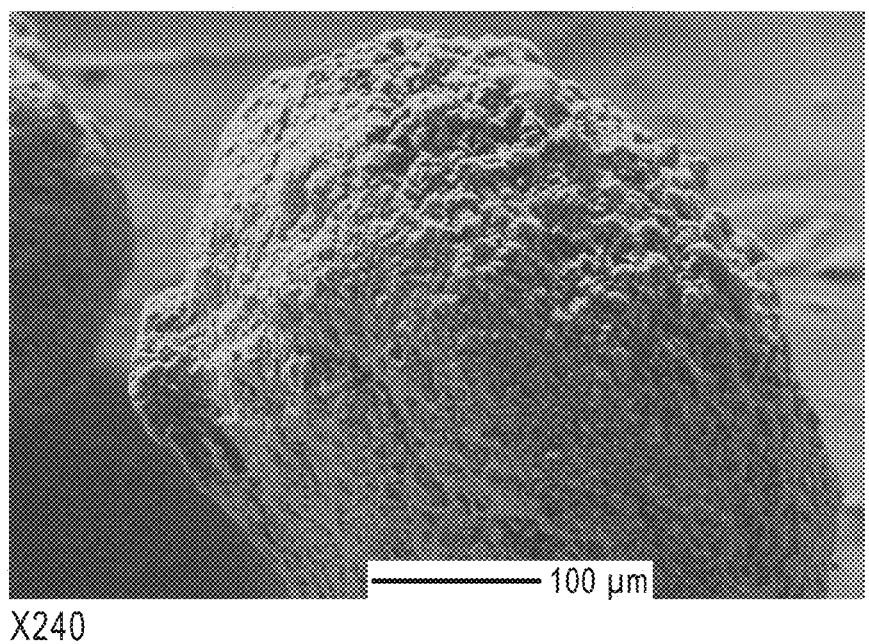
FIG. 18 shows an SEM image of granules prepared as described in Example 13 at 240× magnification.

An active pharmaceutical ingredient can have a particle size distribution, for example, as substantially shown in FIG. 16.

A jet-milled active pharmaceutical ingredient can have a tapped bulk density, for example, less than 0.20 g/mL, less than 0.30 g/mL, less than 0.40 g/mL, or less than 0.50 g/mL.

A jet-milled active pharmaceutical ingredient can have a tapped bulk density, for example, from 0.10 g/mL to 0.30 g/mL, from 0.12 g/mL to 0.28 g/mL, from 0.14 g/mL to 0.26 g/mL, from 0.16 g/mL to 0.24 g/mL, or from 0.18 g/mL to 0.22 g/mL.

A jet-milled active pharmaceutical ingredient can have a particle size distribution characterized, for example, by a D10 from 6 μm to 10 μm, a D50 from 14 μm to 18 μm, and a D90 from 24 μm to 32 μm.

A jet-milled active pharmaceutical ingredient can have a particle size distribution, for example, as substantially shown in FIG. 16.

A pharmaceutical composition provided by the present disclosure can comprise an active pharmaceutical ingredient, a binder, and an antistatic agent.

A granule can comprise a binder or a combination of binders. A granule can comprise, for example, less than 1 wt % of a binder, less than 0.8 wt %, less than 0.6 wt %, less than 0.4 wt %, or less than 0.2 wt % of a binder, where wt % is based on the total weight of the granule. A granule can comprise, for example, from 0.1 wt % to 1.0 wt % of a binder, from 0.2 wt % to 0.9 wt %, from 0.2 wt % to 0.8 wt %, from 0.25 wt % to 0.75 wt %, or from 0.3 wt % to 0.7 wt % of a binder, where wt % is based on the total weight of the granule.

A granule can comprise, for example, less than 1.5 wt % of a binder, less than 1.2 wt %, less than 1.0 wt %, less than 0.8 wt %, or less than 0.6 wt % of a binder, where wt % is based on the total weight of the granule.

A granule can comprise a suitable binder. Examples of suitable binders include natural binders such as starch, pregelatinized starch, sodium alginate, and gelatin; synthetic binders such as polyvinyl pyrrolidone, methylcellulose, hydroxypropylmethyl cellulose, polymethacrylates, sodium carboxy methyl cellulose, and polyethylene glycol; and saccharides such as modified cellulose, hydroxypropyl cellulose, sorbitol, xylitol, and mannitol.

Examples of other suitable binders include, acacia, copovidone, carbomer, corn starch, pregelatinized starch, calcium carboxymethyl cellulose, calcium cellulose glycolate, carmellosum calcium, carboxymethyl cellulose sodium, carmellose sodium, ceratonia, chitosan hydrochloride, dextrates, dextrin, ethyl cellulose, liquid glucose, guar galatomannan, guar gum, hydroxyethyl cellulose, microcrystalline cellulose, hydroxyethylmethyl cellulose, hydroxypropyl cellulose, low-substituted hydroxypropyl cellulose, hydroxypropyl starch, hypromellose/hydroxypropyl methyl cellulose, Methocel®, inulin, magnesium aluminum silicate, maltodextrin, methylcellulose, polyethylene glycol, polyethylene oxide, povidone, sodium alginate, starch, pregelatinized starch, sucrose, compressible sugar, zein, gelatin, polymethacrylates, sorbitol, glucose, and sodium alginate.

A granule can comprise an antistatic agent or a combination of antistatic agents.

A granule can comprise, for example, less than 2 wt % of an antistatic agent, less than 1.25 wt %, less than 1 wt %, less than 0.75 wt %, less than 0.5 wt %, or less than 0.25 wt % of an antistatic agent, where wt % is based on the total weight of the granule. A granule can comprise, for example, from 0.1 wt % to 2.0 wt % of an antistatic agent, from 0.2 wt % to 1.8 wt %, from 0.5 wt % to 1.50 wt %, or from 0.75 wt % to 1.25 wt % of an antistatic agent, where wt % is based on the total weight of the granule.

A granule can comprise a suitable antistatic agent.

Examples of suitable antistatic agents include silica, talc, magnesium stearate, sodium stearyl fumarate, and combinations of any of the foregoing.

An antistatic agent can comprise silica such as hydrophilic silica, such as hydrophilic fumed silica.

An antistatic agent can comprise, for example, hydrophilic fumed silica such as Aerosil® fumed silica from Evonik Industries, Cab-o-sil® fumed silica from Cabot Corporation, or HDK® fumed silica from Brenntag Solutions Group.

An antistatic agent can comprise Aerosil® 200 available from Evonik Industries.

A hydrophilic fumed silica can have a specific surface area (BET from 100 m$^2$/g to 300 m$^2$/g such as from 175 m$^2$/g to 225 m$^2$/g, a pH value from 3.7 to 4.5 in a 4% aqueous dispersion, a loss on drying in 2 hours at 105° C. of less than or equal to 1.5%, a tapped density from about 40 g/L to 60 g/L, and an SiO$_2$ content greater than 99.8% based on ignited material.

In certain granulations, the antistatic agent comprises talc. Pharmaceutical grade talc is available, for example, from Imerys Talc and Elementis PLC. In certain granulations, the antistatic agent does not comprise talc.

A granulation or granule can comprise, for example, from 95.0 wt % to 99.5 wt % of an active pharmaceutical ingredient; from 0.1 wt % to 1.0 wt % of a binder; and from 0.1 wt % to 2.0 wt % of an antistatic agent, wherein wt % is based on the total weight of the granulation or granule.

A granulation or granule can comprise, for example, from 98 wt % to 99 wt % of an active pharmaceutical ingredient; from 0.25 wt % to 0.75 wt % of a binder; and from 0.5 wt % to 1.5 wt % of an antistatic agent, wherein wt % is based on the total weight of the granulation or granule.

A granulation or granule can comprise, for example, from 98.25 wt % to 98.75 wt % of an active pharmaceutical ingredient; from 0.33 wt % to 0.65 wt % of a binder; and from 0.74 wt % to 1.25 wt % of an antistatic agent, wherein wt % is based on the total weight of the granulation or granule.

In addition to an active pharmaceutical ingredient, a binder, and an antistatic agent a granule can comprise one or more excipients such as, for example, flow control agents, lubricants, disintegrants, fillers, compression aids, surfactants, diluents, colorants, buffering agents, glidants, and combinations of any of the foregoing.

A granule can comprise, for example, less than 3 wt % of the one or more excipients, less than 2 wt %, less than 1 wt %, or less than 0.5 wt % of the one or more excipients, where wt % is based on the total weight of the granule. A granule can comprise, for example, from 0 wt % to 3% of one or more excipients, from 0.1 wt % to 3 wt %, from 0.5 wt % to 2 wt % or from 1 wt % to 2 wt % of one or more excipients, where wt % is based on the total weight of the granule.

Examples of suitable flow control agents or glidants include magnesium stearate, fumed silica (colloidal silicon dioxide), starch, talc, and combinations of any of the foregoing.

Examples of suitable lubricants include magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, zinc stearate, and combinations of any of the foregoing.

Examples of suitable disintegrants include citric acid croscarmellose sodium, colloidal silicone dioxide, crospovidone, sodium starch glycolate, microcrystalline cellulose, pregelatinized starch, and combinations of any of the foregoing.

A surfactant can comprise an ionic surfactant or a non-ionic surfactant. Examples of suitable ionic surfactants include docusate sodium (dioctyl sulfosuccinate sodium salt), sodium lauryl sulfate, and combinations of any of the foregoing. Examples of suitable non-ionic surfactants include polyoxyethylene alkyl ethers, polyoxyethylene stearates, poloxamers, polysorbate, sorbitan esters, glyceryl monooleate, and combinations of any of the foregoing.

Examples of suitable fillers and compression aids include lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, sucrose, and combinations of any of the foregoing.

A granulation or granule can consist of an active pharmaceutical ingredient, a binder, and an antistatic agent. In addition to an active pharmaceutical ingredient, a granulation can consist of a binder consisting of hydroxypropyl cellulose and/or an antistatic agent consisting of hydrophilic fumed silica. A granulation or granule can consist of an active pharmaceutical ingredient selected from a compound of Formula (2), a binder wherein the binder consists of hydroxypropyl cellulose, and an antistatic agent wherein the antistatic agent consists of hydrophilic fumed silica. A granulation can have trace amounts of water. In certain granulations, the active pharmaceutical ingredient does not include 4-((L-valyl)oxy)butanoic acid (2a) or a pharmaceutically acceptable salt thereof, the binder does not include hydroxypropylmethyl cellulose, and/or the antistatic agent does not include talc.

A granule provided by the present disclosure can be characterized by a sphericity, for example, from 0.90 to 1, such as from 0.91 to 0.99, or from 0.92 to 0.98, where sphericity is determined using wet dispersion particle shape methods or by dynamic image analysis. A granulation provided by the present disclosure can be characterized by an average sphericity, for example, greater than 0.90, greater than 0.91, greater than 0.92, greater than 0.93, greater than 0.94, or greater than 0.95. A granulation provided by the present disclosure can comprise a plurality of granules characterized by an average sphericity, for example, greater than 0.94, greater than 0.95, greater than 0.96, greater than 0.97, greater than 0.98, or greater than 0.99.

Granules provided by the present disclosure are solid and are characterized by a substantially homogeneous composition throughout the granule.

For high dose active pharmaceutical ingredient, especially when reconstituted in a suspension before administration, to improve palatability it can be useful the granules have a small mean diameter.

A granulation provided by the present disclosure can be characterized, for example, by a particle size distribution D50, for example, from 150 µm to 500 µm, from 150 µm to 450 µm, from 150 µm to 400 µm, from 225 µm to 400 µm, from 150 µm to 350 µm, such as from 175 µm to 325 µm, from 200 µm to 300 µm, or from 225 µm to 275 µm. A granulation can be characterized by a particle size distribution D50, for example, less than 500 µm, less than 450 µm, less than 400 µm, less than 350 µm, less than 300 µm less than 250 µm, or less than 200 µm.

A granulation can be characterized, for example, by a particle size distribution D10 from 50 µm to 150 µm, from 60 µm to 140 µm, from 70 µm, to 120 µm, or from 80 µm to 110 µm. A granulation can be characterized, for example, by a particle size distribution D10 of less than 200 µm, less than 180 µm, less than 160 µm, or less than 140 µm.

A granulation can be characterized, for example, by a particle size distribution D90 from 450 µm to 750 µm, from 475 µm to 725 µm, from 500 µm to 700 µm, from 525 µm to 675 µm, or from 550 µm to 650 µm. A granulation can be characterized, for example, by a particle size distribution of less than 800 µm, less than 700 µm, less than 600 µm, or less than 500 µm.

A granulation can be characterized, for example, by a particle size distribution D10 from 50 µm to 150 µm; a particle size distribution D50 from 220 µm to 320 µm; and a particle size distribution D90 from 480 µm to 560 µm.

A granulation can be characterized, for example, by a particle size distribution D10 from 60 µm to 140 µm; a particle size distribution D50 from 230 µm to 310 µm; and a particle size distribution D90 from 490 µm to 550 µm.

A granulation can be characterized, for example, by a particle size distribution D10 from 70 µm to 130 µm; a particle size distribution D50 from 240 µm to 300 µm; and a particle size distribution D90 from 500 µm to 540 µm.

A granulation can be characterized, for example, by a particle size distribution D10 from 70 µm to 230 µm; and a particle size distribution D90 from 400 µm to 750 µm.

A granulation can be characterized, for example, by a particle size distribution D10 from 80 µm to 120 µm; and a particle size distribution D90 from 510 µm to 650 µm.

An example of a particle size distribution for a granulation provided by the present disclosure is shown in FIG. 9A.

A particle size distribution can be determined by laser diffraction or by sieve analysis.

A granulation can have a bulk density, for example, greater than 0.40 g/mL, greater than 0.50 g/mL, greater than 0.60 g/mL, greater than 0.90 g/mL, greater than 1.10 g/mL, greater than 1.30 g/mL, or greater than 1.50 g/mL.

A granulation can have a bulk density, for example, from 0.40 g/mL to 1.60 g/mL, from 0.40 g/mL to 1.20 g/mL, from 0.40 g/mL to 0.80 g/mL, from 0.50 g/mL to 1.60 g/mL, from 0.50 g/mL to 1.40 g/mL, from 0.50 g/mL to 1.20 g/mL, from 0.60 g/mL to 1.60 g/mL, from 0.70 g/mL to 1.50 g/mL, from 0.80 g/mL to 1.40 g/mL, or from 1.00 g/mL to 1.20 g/mL. A granulation can have a bulk density, for example, from 0.5 g/mL to 0.8 g/mL, from 0.55 g/mL to 0.75 g/mL, or from 0.6 g/mL to 0.7 g/mL.

Bulk density can be determined using a bulk density cylinder.

Scanning electron micrograph (SEM) images of examples of granules provided by the present disclosure are shown in FIGS. 9B-9C with magnifications of 110×, 220×, 1,000×, and 2,000×, respectively. The granules shown in FIGS. 9B-9E are characterized by substantially smooth surfaces.

Smooth granule surfaces facilitate the ability to coat the granules with a thin, continuous coating having a substantially homogeneous thickness. The qualities of the coating can be important for controlled release formulations. For example, rough and/or porous surfaces tend to require a significantly higher amount of coating to achieve a comparable release profile to smooth surfaces. In addition, coatings of rough and/or porous surfaces can lead to variable dissolution or release profile.

A granulation provided by the present disclosure, when dried, can be characterized by a loss on drying (LOD), for example, from 0.05 wt % to 1.5 wt %, from 0.1 wt % to 1.4 wt %, from 0.2 wt % to 1.2 wt %, from 0.2 wt % to 1.3 wt %, from 0.3 wt % to 1.2 wt %, from 0.7 wt % to 1.1 wt %, from 0.92 wt % to 0.98 wt %, from 0.93 wt % to 0.97 wt %, or from 0.94 wt % to 0.96 wt %, where wt % is based on the total weight of the granulation. A granulation provided by the present disclosure, when dried, can be characterized by a loss on drying (LOD), for example, of less than 1.5 wt %, less than 1.3 wt %, less than 1.1 wt %, less than 0.9 wt %, less than 0.7 wt %, less than 0.5 wt %, or less than 0.1 wt %, where wt % is based on the total weight of the granulation. The LOD represents removal of water incorporated into the granules during preparation of the granulation and after drying.

LOD is determined by thermogravimetric analysis.

A granulation provided by the present disclosure can be characterized by a friability value, for example, from 0 wt % to 2 wt % such as less than 2 wt %, less than 1.5 wt %, less than 1 wt %, or less than 0.5 wt %, where wt % is based on the total weight of the granulation. A granulation provided by the present disclosure can be characterized by a friability value, for example, from 0.1 wt % to 2 wt %, from 0.2 wt % to 1.8 wt %, from 0.2 wt % to 1.6 wt %, from 0.4 wt % to 1.2 wt %, or from 0.6 wt % to 1.2 wt %, where wt % is based on the total weight of the granulation. Granules with low friability are easier to coat than are granules with high friability. Friability is defined as the amount (wt %) of granules having a diameter less than 75 μm that are generated by subjecting a granulation to a sonic sifter operated at a vibration amplitude of 8 corresponding to 3,600 sonic energy pulses per minute for at least 2 minutes.

A granulation provided by the present disclosure can have a friability, for example, of less than 1.02% where friability is determined using a sonic sifter.

Granulations provided by the present disclosure can be prepared by combining an active pharmaceutical ingredient and one or more excipients to form a dry mixture, wet granulating the dry mixture to provide a wet granulation, and wet massing the wet granulation to provide the granulation. The steps of wet granulating and wet massing can be repeated one or more times, such as from 1 to 6 times, such as 1, 2, 3, 4, 5, 6, or more times.

A dry mixture can comprise, for example, an active pharmaceutical ingredient, a binder, and an antistatic agent.

A dry mixture can comprise an active pharmaceutical ingredient or a combination of active pharmaceutical ingredient. A dry mixture can comprise greater than 95 wt % of an active pharmaceutical ingredient, greater than 96 wt %, greater than 97 wt %, greater than 98 wt % or greater than 99 wt % of an active pharmaceutical ingredient, where wt % is based on the total weight of the dry mixture. A dry mixture can comprise, for example, from 95 wt % to 99.5 wt % of an active pharmaceutical ingredient, from 96 wt % to 99 wt %, from 97 wt % to 99 wt %, or from 98 wt % to 99 wt % of an active pharmaceutical ingredient, where wt % is based on the total weight of the dry mixture.

A dry mixture can comprise a binder or a combination of binders. A dry mixture can comprise, for example, less than 3 wt %, less than 2.5 wt %, less than 2 wt %, less than 1.5 wt %, less than 1 wt % of a binder, less than 0.8 wt %, less than 0.6 wt %, less than 0.4 wt %, or less than 0.2 wt % of a binder, where wt % is based on the total weight of the dry mixture. A dry mixture can comprise, for example, from 0.1 wt % to 3.0 wt % of a binder, from 0.1 wt % to 2.0 wt %, from 0.1 wt % to 1.5 wt %, from 0.2 wt % to 0.9 wt %, from 0.2 wt % to 0.8 wt %, from 0.25 wt % to 0.75 wt %, or from 0.3 wt % to 0.7 wt % of a binder, where wt % is based on the total weight of the dry mixture.

A dry mixture can comprise, for example, less than 3 wt % of an antistatic agent, less than 2 wt %, less than 1.25 wt %, less than 1 wt %, less than 0.75 wt %, less than 0.5 wt %, or less than 0.25 wt % of an antistatic agent, where wt % is based on the total weight of the dry mixture. A dry mixture can comprise, for example, from 0.1 wt % to 2.0 wt % of an antistatic agent, from 0.2 wt % to 1.75 wt %, from 0.5 wt % to 1.50 wt %, or from 0.75 wt % to 1.25 wt % of an antistatic agent, where wt % is based on the total weight of the dry mixture.

A dry mixture can comprise, for example, from 95.0 wt % to 99.5 wt % of an active pharmaceutical ingredient; from 0.1 wt % to 1.0 wt % of a binder; and from 0.1 wt % to 2.0 wt % of an antistatic agent, wherein wt % is based on the total weight of the dry mixture.

A dry mixture can comprise, for example, from 98 wt % to 99 wt % of an active pharmaceutical ingredient; from 0.25 wt % to 0.75 wt % of a binder; and from 0.5 wt % to 1.5 wt % of an antistatic agent, wherein wt % is based on the total weight of the dry mixture.

A dry mixture can comprise, for example, from 98.25 wt % to 98.75 wt % of an active pharmaceutical ingredient; from 0.33 wt % to 0.65 wt % of a binder; and from 0.74 wt % to 1.25 wt % of an antistatic agent, wherein wt % is based on the total weight of the dry mixture.

An active pharmaceutical ingredient can be screened, de-lumped, co-milled, Fitz-milled, pin-milled, or jet-milled before adding to the dry mixture.

An active pharmaceutical ingredient can have a size distribution characterized by a D90, for example, less than 30 μm, less than 25 μm, less than 20 μm, or less than 15 μm. An active pharmaceutical ingredient can have a size distribution characterized by a D90, for example, from 10 μm to 30 μm, from 11 μm to 25 μm, or from 10 μm to 20 μm. An as-crystallized active pharmaceutical ingredient can be jet-milled to provide a suitable particle size distribution.

The dry mixture can be mixed in a bowl, for example, for from 0.5 minutes to 5 minutes to provide a homogeneous dry mixture.

Granulating can comprise the steps of (a) granulating the dry mixture to provide a dry granulation; and (b) adding water to the dry granulation and granulating to provide a wet granulation.

Granulating the dry mixture can comprise, for example, granulating for from 5 minutes to 20 minutes such as from 5 minutes to 15 minutes, or from 5 minutes to 10 minutes, at a mixer speed, for example, from 700 rpm to 1000 rpm, such as from 800 rpm to 900 rpm; and a chopper speed, for example, from 3,000 rpm to 4200 rpm, such as from 3,200 rpm to 4,000 rpm, or from 3,400 rpm to 3,800 rpm.

The dry granulation obtained in step (a) can be wet granulated.

During wet granulation, water can be added to the dry granulation at a rate, for example, from 0.0025 wt %/min to 0.0075 wt %/min, where wt % is based on the total weight of the dry granulation. The wet granulation can be granulated, for example, for from 5 minutes to 20 minutes, such as from 5 minutes to 15 minutes, or from 5 minutes to 10 minutes. During wet granulation the mixer speed can be, for example, from 700 rpm to 1000 rpm, such as from 800 rpm to 900 rpm; and the chopper speed can be, for example, from 3,000 rpm to 4200 rpm, such as from 3,200 rpm to 4,000 rpm, or from 3,400 rpm to 3,800 rpm.

At the end of the process, the wet granulation can contain, for example, from 3 wt % to 7 wt % water, such as from 3.5 wt % to 6.5 wt %, or from 4 wt % water to 6 wt % water, where wt % is based on the total weight of the wet granulation.

The amount of water added is determined by weighing the amount of water incorporated into/consumed by the granulation.

During wet granulation the temperature of the wet granulation can be maintained, for example, from 20° C. to 25° C.

The wet granulation can then be wet massed to form smooth and high-density granules.

Wet massing can be done, for example, at a mixer speed from 400 rpm to 700 rpm such as from 500 rpm to 600 rpm, and a chopper speed, for example, from 1300 rpm to 2300 rpm such as from 1500 rpm to 2100 rpm; for from 20 minutes to 100 minutes such as from 30 minutes to 90 minutes, from 30 minutes to 80 minutes, or from 30 minutes to 60 minutes.

During wet massing the temperature of the wet granulation can be maintained at a temperature, for example, from 20° C. to 25° C. such as from 22° C. to 25° C. The temperature of the wet granulation can be maintained, for example, by immersing the mixing bowl containing the granulation in a temperature-controlled bath.

Wet massing can be done, for example, using a granulation bowl with a mixer speed from 525 rpm to 575 rpm, and a chopper speed from 1700 rpm to 1900 rpm for from 20 minutes to 80 minutes such as from 25 minutes to 70 minutes, from 30 minutes to 60 minutes, or from 35 minutes to 55 minutes, at a temperature from 22° C. to 24° C.

During wet massing, the wet granulation can comprise, for example, from 0.01 wt % to 0.1 wt % water, from 0.02 wt % to 0.085 wt %, from 0.025 wt % to 0.075 wt %, or from 0.035 wt % to 0.065 wt % water, where water is based on the total weight of the wet granulation.

After wet massing, the granulation can be dried.

The granulation can be dried in an oven or in a fluid bed dryer until the loss on drying is less than 1.0 w/wt %.

A granulation prepared by a method provided by the present disclosure can be characterized by a yield in the particle size range from 100 µm to 425 µm of 55 wt % to 70 wt %; a yield in the particle size range from 100 µm to 425 µm of 63 wt %; a yield in the particle size range from 200 µm to 350 µm of from 30 wt % to 40 wt %; and by a yield in the particle size range from 200 µm to 350 µm of 36 wt %, wherein the particle size range is determined by sieve analysis and wt % is based on the total weight of the granulation.

In certain methods for preparing granulations provided by the present disclosure, the active pharmaceutical ingredient can have a particle size distribution D50, for example, less than 30 µm, less than 25 µm, or less than 20 µm. The active pharmaceutical ingredient can have a specific gravity, for example, form 200 m2/kg to 1200 m2/kg.

During the one or more granulation steps, the temperature of the granulation can be maintained at a temperature, for example for 20° C. to 25° C. It can be desirable that water be added to the granulation at the lowest possible rate such as at a rate of less than 2 g/min. Adding water slowly can minimize agglomeration. During the one or more granulation steps from about 5 wt % to 25 wt %, such as from 10 wt % to 20 wt % total water can be added, where wt % is based on the total weight of the active pharmaceutical ingredient. During each of the one or more granulation steps it can be useful to maintain the mixer speed as high as possible such as greater than 600 rpm, greater than 700 rpm, greater than 800 rpm, or greater than 1000 rpm.

During the one or more wet massing steps the temperature of the granulation can be maintained, for example, at a temperature form 15° C. to 25° C. During each of the one or more wet massing steps it can be useful to maintain the mixer speed as high as possible such as greater than 600 rpm, greater than 700 rpm, greater than 800 rpm, or greater than 1000 rpm.

The granulation and wet massing steps until the granulation exhibit a desired bulk density and/or until the bulk density of the granulation does not significantly increase. For example, the granulation can be considered complete when the bulk density of the granulation increases by less than 10% or less than 5% following the last wet massing step. The granulation and wet massing steps can be repeated until the bed height does not significantly decrease after the last wet massing step.

A granule provided by the present disclosure can comprise one or more coatings.

A coating can have an average thickness, for example, less than 300 µm, less than 200 µm, less than 150 µm, less than 100 µm, less than 50 µm, or less than 25 µm.

A coated granule can comprise, for example, less than 50 wt % of a coating, less than 40 wt %, less than 30 wt %, less than 20 wt %, or less than 10 wt % of a coating, where wt % is based on the total weight of the coated granule. Dosage forms containing a highly water-soluble active pharmaceutical ingredient require a thick coating to reduce the release rate of the active pharmaceutical ingredient.

A coating can comprise a pharmaceutically acceptable polymer, a plasticizing agent, an anti-tacking agent, a colorant or pigment, a glidant, and a viscosity modifier.

For example, a coating can comprise an immediate release coating, or a controlled-release coating. A controlled-release coating can comprise, for example, a delayed release coating, a pH-release coating, a sustained release coating, or a modified-release coating. A delayed release drug delivery system is designed to deliver drugs at a specified time or over a period of time following administration.

A coating can comprise a water-soluble coating and can include polymers such as polyvinyl alcohol, hydroxypropylmethyl cellulose, polyvinylpyrrolidone, hydroxypropyl cellulose, hydroxypropyl ethyl cellulose, polyethylene glycol, hydroxyethyl cellulose, and combinations of any of the foregoing.

A coating can comprise a water-insoluble coating or water-resistant coating to protect a dosage form from absorbing water during storage. Examples of suitable water-insoluble or water-resistant coatings can include polymers such as ethyl cellulose, poly-acrylates, polymethacrylates, and combinations of any of the foregoing.

A coating can provide, for example a time-dependent release, a pH-dependent release, or sustained release.

A coating can be applied to granules provided by the present disclosure by any suitable method such as by spraying a solution, suspension, or dispersion of the coating onto granules in a fluidized bed apparatus.

A pharmaceutical composition provided by the present disclosure can comprise a granulation provided by the present disclosure.

A pharmaceutical composition can comprise any suitable dosage form for oral administration.

Examples of suitable oral dosage forms include tablets, capsules, caplets, sachets, bottles, stick packs, and suspensions.

An oral dosage form can comprise, for example, from 0.1 grams to 10 grams of an active pharmaceutical ingredient, from 0.2 grams to 8 grams, from 0.5 grams to 5 grams, from 1 gram to 4.5 grams, or from 1.5 grams to 4 grams of an active pharmaceutical ingredient. An oral dosage form can comprise, for example, greater than 0.5 grams, greater than 1 gram, greater than 2 grams, greater than 3 grams, greater than 4 grams, greater than 6 grams, or greater than 8 grams of an active pharmaceutical ingredient.

An oral formulation provided by the present disclosure can comprise an oral tablet formulation.

An oral formulation provided by the present disclosure can comprise an oral suspension.

ASPECTS OF THE INVENTION

The invention is further defined by the following aspects.

Aspect 1. A granulation comprising a plurality of granules, wherein the granules are characterized by greater than 95 wt % of an active pharmaceutical ingredient (API), wherein, the granulation is characterized by a particle size distribution (PSD) (D50) from 150 μm to 300 μm; and wt % is based on the total weight of the granulation.

Aspect 2. The granulation of aspect 1, wherein the granulation comprises from 98 wt % to 99 wt % of the active pharmaceutical ingredient, wherein wt % is based on the total weight of the granulation.

Aspect 3. The granulation of any one of aspects 1 to 2, wherein the granulation is characterized by a PSD (D50) from 225 μm to 275 μm.

Aspect 4. The granulation of any one of aspects 1 to 3, wherein the granulation is characterized by a friability less than 2 wt %, wherein wt % is based on the total weight of the granulation.

Aspect 5. The granulation of any one of aspects 1 to 4, wherein the granulation is characterized by: a PSD (D10) from 50 μm to 150 μm; and a PSD (D90) from 450 μm to 750 μm, wherein the PSD is determined by sieve analysis.

Aspect 6. The granulation of any one of aspects 1 to 4, wherein the granulation is characterized by: a PSD (D10) from 80 μm to 120 μm; and a PSD (D90) from 510 μm to 650 μm, wherein the PSD is determined by sieve analysis.

Aspect 7. The granulation of any one of aspects 1 to 4, wherein the granulation is characterized by a PSD (D10) of 106 μm; a PSD (D50) of 267 μm; and a PSD (D90) of 533 μm, wherein the PSD is determined by sieve analysis.

Aspect 8. The granulation of any one of aspects 1 to 7, wherein the granulation has an active pharmaceutical ingredient bulk density from 0.150 g/mL to 0.320 g/mL, wherein bulk density is determined using USP 616, Method I.

Aspect 9. The granulation of any one of aspects 1 to 2, wherein the granulation has an active pharmaceutical ingredient bulk density of 0.250 g/mL to 0.280 g/mL, wherein bulk density is determined using USP 616, Method I.

Aspect 10. The granulation of any one of aspects 1 to 7, wherein the granulation has a bulk density from 0.70 g/mL to 1.70 g/mL, wherein bulk density is determined using USP 616, Method I.

Aspect 11. The granulation of any one of aspects 1 to 10, wherein the granulation is characterized by a loss on drying (LOD) from 0 wt % to 1.5 wt %, where wt % is based on the weight of the granulation after drying.

Aspect 12. The granulation of any one of aspects 1 to 10, wherein the granulation is characterized by a loss on drying (LOD) from 0.2 wt % to 1.2 wt %, where wt % is based on the weight of the granulation after drying.

Aspect 13. The granulation of any one of aspects 1 to 12, wherein the granulation is characterized by a friability from 0.95% to 1.10%, wherein friability is determined using a sieve shaker as described in the examples.

Aspect 14. The granulation of any one of aspects 1 to 12, wherein the granulation is characterized by a friability of 1.02%, wherein friability is determined using a sieve shaker as described in the examples.

Aspect 15. The granulation of any one of aspects 1 to 14, wherein the granules are characterized by a sphericity from 0.90 to 1.00, wherein sphericity is determined by dynamic image analysis.

Aspect 16. The granulation of any one of aspects 1 to 14, wherein the granules characterized by a surface roughness as substantially shown in FIGS. 9B-9E.

Aspect 17. The granulation of any one of aspects 1 to 15, wherein the active pharmaceutical ingredient has an aqueous solubility greater than 100 mg/mL.

Aspect 18. The granulation of any one of aspects 1 to 15, wherein the active pharmaceutical ingredient has an aqueous solubility from 100 mg/mL to 1,000 mg/mL.

Aspect 19. The granulation of any one of aspects 1 to 18, wherein the active pharmaceutical ingredient comprises γ-hydroxybutyric acid or a pharmaceutically acceptable salt thereof.

Aspect 20. The granulation of any one of aspects 1 to 18, wherein the active pharmaceutical ingredient comprises γ-hydroxybutyric acid, a derivative of γ-hydroxybutyric acid or a pharmaceutically acceptable salt of any of the foregoing.

Aspect 21. The granulation of any one of aspects 1 to 18, wherein the active pharmaceutical ingredient comprises a compound of Formula (2):

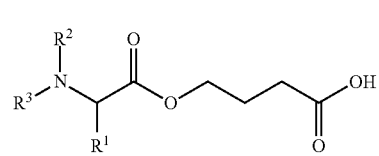

(2)

or a pharmaceutically acceptable salt thereof, wherein,
R$^1$ is selected from hydrogen and C$_{1-6}$ alkyl; and
each of R$^2$ and R$^3$ is independently selected from hydrogen, C$_{1-6}$ alkyl, C$_{1-6}$ alkoxylcarbonyl, and C$_{3-6}$ cycloalkoxylcarbonyl.

Aspect 22. The granulation of aspect 21, wherein the active pharmaceutical ingredient is selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

Aspect 23. The granulation of aspect 21, wherein the active pharmaceutical ingredient is 4-((L-valyl)oxy)butanoic acid (2a) or a pharmaceutically acceptable salt thereof:

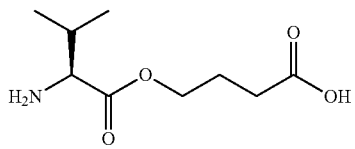

(2a)

Aspect 24. The granulation of any one of aspects 1 to 23, wherein the granulation further comprises: a binder; and an antistatic agent.

Aspect 25. The granulation of aspect 24, wherein the granulation comprises: from 98 wt % to 99 wt % of the active pharmaceutical ingredient; from 0.25 wt % to 0.75 wt % of a binder; and from 0.5 wt % to 1.5 wt % of an antistatic agent, wherein wt % is based on the total weight of the granulation.

Aspect 26. The granulation of aspect 24, wherein the granulation comprises: 98.5 wt % of the active pharmaceutical ingredient; 0.5 wt % of a binder; and 1.0 wt % of an antistatic agent, wherein wt % is based on the total weight of the granulation.

Aspect 27. The granulation of any one of aspects 24 to 26, wherein the binder comprises hydroxypropyl cellulose.

Aspect 28. The granulation of any one of aspects 24 to 27, wherein the antistatic agent comprises hydrophilic fumed silica.

Aspect 29. The granulation of any one of aspects 1 to 28, wherein the granules comprise a coating.

Aspect 30. The granulation of aspect 29, wherein the granulation comprises less than 2 wt % of the coating, wherein wt % is based on the total weight of the granulation.

Aspect 31. The granulation of any one of aspects 29 to 30, wherein the coated granules comprise greater than 95 wt % of the active pharmaceutical ingredient, wherein wt % is based on the total weight of the granules.

Aspect 32. The granulation of any one of aspects 29 to 31, wherein the coating comprises a controlled release coating.

Aspect 33. A pharmaceutical composition comprising the granulation of any one of aspects 1 to 32.

Aspect 34. The pharmaceutical composition of aspect 33, wherein the pharmaceutical composition comprises an oral formulation.

Aspect 35. The pharmaceutical composition of any one of aspects 33 to 34, wherein the pharmaceutical composition comprises an immediate release formulation.

Aspect 36. The pharmaceutical composition of any one of aspects 33 to 34, wherein the pharmaceutical composition comprises a controlled release formulation.

Aspect 37. A method of preparing the granulation of any one of aspects 1 to 32, comprising: combining the active pharmaceutical ingredient, a binder, and an antistatic agent to form a dry mixture; wet granulating the dry mixture for from 5 minutes to 10 minutes to provide a wet granulation; wet massing the wet granulation for from 30 minutes to 60 minutes to provide a wet granulation; and drying the wet granulation to provide the granulation.

Aspect 38. The method of aspect 37, wherein wet granulating comprises: granulating the dry mixture for from 5 minutes to 15 minutes at a mixer speed from 800 rpm to 900 rpm and a chopper speed from 3200 rpm to 4000 rpm; adding water at a rate from 0.0025 wt %/min to 0.0075 wt %/min, wherein wt % is based on the total weight of the dry mixture; and maintaining the temperature of the wet granulation during wet granulation at a temperature from 20° C. to 25° C.

Aspect 39. The method of aspect 37, wherein wet granulating comprises: granulating for from 5 minutes to 60 minutes at a mixer speed of 850 rpm and a chopper speed from 3600 rpm; adding water at a rate of 0.005 wt %/min, wherein wt % is based on the total weight of the mixture; and maintaining the temperature of the wet granulation from 22° C. to 24° C.

Aspect 40. The method of any one of aspects 37 to 39, wherein wet massing comprises: wet massing for from 30 minutes to 60 minutes at a mixer speed of 550 rpm and a chopper speed from 1,500 rpm to 2,100 rpm; and maintaining the temperature of the wet granulation at a temperature from 20° C. to 25° C.

Aspect 41. The method of any one of aspects 37 to 39, wherein wet massing comprises: wet massing for from 30 minutes to 60 minutes at a mixer speed from 500 rpm to 600 rpm and a chopper speed from 1800 rpm; and maintaining the temperature of the wet granulation from 22° C. to 24° C.

Aspect 42. The method of any one of aspects 37 to 41, wherein the mixture comprises: from 98 wt % to 99 wt % of the active pharmaceutical ingredient; from 0.25 wt % to 0.75 wt % of a binder; and from 0.5 wt % to 1.5 wt % of an antistatic agent, wherein wt % is based on the total weight of the mixture.

Aspect 43. The method of any one of aspects 37 to 41, wherein the mixture comprises: 98.5 wt % of the active pharmaceutical ingredient; 0.5 wt % of a binder; and 1.0 wt % of an antistatic agent, wherein wt % is based on the total weight of the mixture.

Aspect 44. The method of any one of aspects 37 to 43, wherein the granulation is characterized by a yield in the particle size range from 100 μm to 425 μm of 55 wt % to 70 wt %, wherein the particle size range is determined by laser diffraction and wt % is based on the total weight of the granulation.

Aspect 45. The method of any one of aspects 37 to 44, wherein the granulation is characterized by a yield in the particle size range from 100 μm to 425 μm of 63 wt %, wherein the particle size range is determined by laser diffraction and wt % is based on the total weight of the granulation.

Aspect 46. The method of any one of aspects 37 to 45, wherein the granulation is characterized by a yield in the particle size range from 200 μm to 350 μm of from 30 wt % to 40 wt %, wherein the particle size range is determined by laser diffraction and wt % is based on the total weight of the granulation.

Aspect 47. The method of any one of aspects 37 to 46, wherein the granulation is characterized by a yield in the particle size range from 200 μm to 350 μm of 36 wt %, wherein the particle size range is determined by laser diffraction and wt % is based on the total weight of the granulation.

Aspect 48. The method of any one of aspects 37 to 47, wherein the wet granulation comprises from 0.025 wt % to 0.075 wt % water, wherein wt % is based on the total weight of the wet granulation.

Aspect 49. The method of any one of aspects 37 to 47, wherein the wet granulation comprises 0.05 wt % water, wherein wt % is based on the total weight of the wet granulation.

Aspect 1A. A granulation comprising a plurality of granules, wherein, the granules comprise greater than 95 wt % of an active pharmaceutical ingredient (API), wherein wt % is based on the total weight of the granulation; and the active pharmaceutical ingredient comprises an aqueous solubility greater than 100 mg/mL.

Aspect 2A. The granulation of aspect 1A, wherein the active pharmaceutical ingredient is characterized by a particle size distribution characterized by a D90 less than 30 µm.

Aspect 3A. The granulation of any one of aspects 1A to 2A, wherein the active pharmaceutical ingredient is characterized by a specific surface area from 200 m²/kg to 1200 m²/kg, wherein the specific surface area is determined using laser diffraction.

Aspect 4A. The granulation of any one of aspects 1A to 3A, wherein the active pharmaceutical ingredient is characterized by a bulk density from 0.1 g/mL to 0.4 g/mL, wherein the bulk density is determined according to USP 616, Method 1.

Aspect 5A. The granulation of any one of aspects 1A to 4A, wherein the active pharmaceutical ingredient has a bulk density from 0.15 g/mL to 0.35 g/mL, wherein the bulk density is determined using USP 616, Method I.

Aspect 6A. The granulation of any one of aspects 1A to 5A, wherein the active pharmaceutical ingredient has an aqueous solubility from 100 mg/mL to 1,000 mg/mL.

Aspect 7A. The granulation of any one of aspects 1A to 6A, wherein the granules comprise from 96 wt % to 99.5 wt % of the active pharmaceutical ingredient, wherein wt % is based on the total weight of the granules.

Aspect 8A. The granulation of any one of aspects 1A to 7A, wherein the granulation is characterized by a particle size distribution (PSD) characterized by a D50 from 150 µm to 500 µm, wherein the particle size distribution is determined by laser diffraction or by sieve analysis.

Aspect 9A. The granulation of any one of aspects 1A to 7A, wherein the granulation is characterized by a particle size distribution D50 from 200 µm to 400 µm, wherein the particle size distribution is determined by laser diffraction or by sieve analysis Aspect 10A. The granulation of any one of aspects 1A to 7A, wherein the granulation is characterized by: a particle size distribution D10 from 50 µm to 250 µm; and a particle size distribution D90 from 400 µm to 750 µm, wherein the particle size distribution is determined by laser diffraction or by sieve analysis.

Aspect 11A. The granulation of any one of aspects 1A to 7A, wherein the granulation is characterized by a particle size distribution D10 from 80 µm to 120 µm; and a particle size distribution D90 from 510 µm to 650 µm, wherein the particle size distribution is determined by laser diffraction or by sieve analysis.

Aspect 12A. The granulation of any one of aspects 1A to 11A, wherein the granulation has a bulk density from 0.50 g/mL to 1.20 g/mL, wherein bulk density is determined according to USP 616, Method I.

Aspect 13A. The granulation of any one of aspects 1A to 12A, wherein the granulation has a bulk density from 0.40 g/mL to 0.80 g/mL, wherein bulk density is determined according to USP 616, Method I.

Aspect 14A. The granulation of any one of aspects 1A to 13A, wherein the granulation is characterized by a loss on drying (LOD) from 0.05 wt % to 1.5 wt %, where wt % is based on the weight of the granulation after drying.

Aspect 15A. The granulation of any one of aspects 1A to 13A, wherein the granulation is characterized by a loss on drying (LOD) from 0.2 wt % to 1.2 wt %, where wt % is based on the weight of the granulation after drying.

Aspect 16A. The granulation of any one of aspects 1A to 15A, wherein the granulation is characterized by a friability less than 2 wt %, wherein wt % is based on the total weight of the granulation, and the friability is determined using a sieve shaker according to the method described in the examples.

Aspect 17A. The granulation of any one of aspects 1A to 15A, wherein the granulation is characterized by a friability less than 1.10 wt %, wherein wt % is based on the total weight of the granulation, and the friability is determined using a sieve shaker according to the method described in the examples.

Aspect 18A. The granulation of any one of aspects 1A to 15A, wherein the granulation is characterized by a friability of less than 1.02 wt %, wherein wt % is based on the total weight of the granulation, and the friability is determined using a sieve shaker according to the method described in the examples.

Aspect 19A. The granulation of any one of aspects 1A to 18A, wherein the granules are characterized by a sphericity from 0.90 to 1.00, wherein sphericity is determined by dynamic image analysis.

Aspect 20A. The granulation of any one of aspects 1A to 19A, wherein the granules are characterized by a surface roughness as substantially shown in FIGS. 9B-9E.

Aspect 21A. The granulation of any one of aspects 1A to 19A, wherein the granules are characterized by a surface roughness as substantially shown in FIGS. 19-20.

Aspect 22A. The granulation of any one of aspects 1A to 21A, wherein the active pharmaceutical ingredient comprises γ-hydroxybutyric acid or a pharmaceutically acceptable salt thereof.

Aspect 23A. The granulation of any one of aspects 1A to 21A, wherein the active pharmaceutical ingredient comprises a derivative of γ-hydroxybutyric acid or a pharmaceutically acceptable salt thereof.

Aspect 24A. The granulation of any one of aspects 1A to 21A, wherein the active pharmaceutical ingredient comprises a compound of Formula (2):

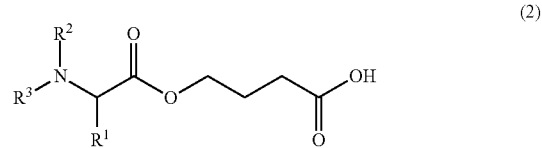

or a pharmaceutically acceptable salt thereof, wherein,
$R^1$ is selected from hydrogen and $C_{1-6}$ alkyl; and
each of $R^2$ and $R^3$ is independently selected from hydrogen, $C_{1-6}$ alkyl, $C_{1-6}$ alkoxylcarbonyl, and $C_{3-6}$ cycloalkoxylcarbonyl.

Aspect 25A. The granulation of any one of aspects 1A to 21A, wherein the active pharmaceutical ingredient is selected from:
4-(((tert-butoxycarbonyl)glycyl)oxy)butanoic acid;
4-(glycyloxy)butanoic acid;
4-((D-valyl)oxy)butanoic acid;
4-((L-alanyl)oxy)butanoic acid;
4-(((ethoxycarbonyl)glycyl)oxy)butanoic acid;
4-(((isopropoxycarbonyl)glycyl)oxy)butanoic acid;
4-((((cyclohexyloxy)carbonyl)glycyl)oxy)butanoic acid;
4-(((ethoxycarbonyl)-D-valyl)oxy)butanoic acid;
4-((L-valyl)oxy)butanoic acid;
a pharmaceutically acceptable salt of any of the foregoing; and
a combination of any of the foregoing.

Aspect 26A. The granulation of any one of aspects 1A to 21A, wherein the active pharmaceutical ingredient is 4-((L-valyl)oxy)butanoic acid (2a) or a pharmaceutically acceptable salt thereof:

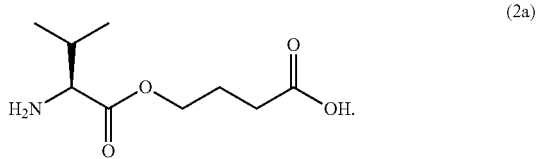

(2a)

Aspect 27A. The granulation of any one of aspects 1A to 26A, wherein the granules further comprise: a binder; and an antistatic agent.

Aspect 28A. The granulation of aspect 27A, wherein the granules comprise no more than 2 wt % of the binder, wherein wt % is based on the total weight of the granules.

Aspect 29A. The granulation of any one of aspects 27A to 28A, wherein the granules comprise no more than 1.5 wt % of the antistatic agent, wherein wt % is based on the total weight of the granules.

Aspect 30A. The granulation of any one of aspects 27A to 29A, wherein the granules comprise: from 98 wt % to 99 wt % of the active pharmaceutical ingredient; from 0.25 wt % to 0.75 wt % of a binder; and from 0.5 wt % to 1.5 wt % of an antistatic agent, wherein wt % is based on the total weight of the granules.

Aspect 31A. The granulation of any one of aspects 27A to 29A, wherein the granules comprise: greater than 98.5 wt % of the active pharmaceutical ingredient; less than or equal to 0.5 wt % of a binder; and less than or equal to 1.0 wt % of an antistatic agent, wherein wt % is based on the total weight of the granules.

Aspect 32A. The granulation of any one of aspects 27A to 31A, wherein the binder comprises hydroxypropyl cellulose.

Aspect 33A. The granulation of aspect 32A, wherein the hydroxypropyl cellulose comprises a size distribution characterized by a D10 from 10 μm to 35 μm; a D50 from 45 μm to 90 μm; and a D90 from 100 μm to 300 μm.

Aspect 34A. The granulation of any one of aspects 32A to 33A, wherein the hydroxypropyl cellulose comprises a weight average molecular weight from 50,000 Daltons to 110,000 Daltons.

Aspect 35A. The granulation of any one of aspects 32A to 34A, wherein the hydroxypropyl cellulose comprises a viscosity from 300 mPa×sec to 600 mPa×sec ss determined using a Brookfield viscometer with at 25° C.

Aspect 36A. The granulation of any one of aspects 30A to 35A, wherein the antistatic agent comprises hydrophilic fumed silica.

Aspect 37A. The granulation of aspect 36A, wherein the hydrophilic fumed silica has an $SiO_2$ content greater than 99.8% based on ignited material.

Aspect 38A. The granulation of any one of aspects 36A to 37A, wherein the hydrophilic fumed silica has a specific surface area (BET) from 175 $m^2$/g to 225 $m^2$/g.

Aspect 39A. The granulation of any one of aspects 36A to 37A, wherein the hydrophilic fumed silica has a pH value from 3.7 to 4.5 in a 4% aqueous dispersion.

Aspect 40A. The granulation of any one of aspects 36A to 37A, wherein the hydrophilic fumed silica has a LOD of less than 1.5 wt %.

Aspect 41A. The granulation of any one of aspects 36A to 37A, wherein the hydrophilic fumed silica has a tapped density from 30 g/L to 70 g/L.

Aspect 42A. The granulation of any one of aspects 1A to 41A, wherein the granules comprise a coating.

Aspect 43A. The granulation of aspect 42A, wherein the granules comprise from 1 wt % to 10 wt % of the coating, wherein wt % is based on the total weight of the granules.

Aspect 44A. The granulation of any one of aspects 42A to 43A, wherein the coating comprises a seal coating, a controlled release coating, or a combination thereof.

Aspect 45A. A pharmaceutical composition comprising the granulation of any one of aspects 1A to 44A.

Aspect 46A. The pharmaceutical composition of aspect 45A, wherein the pharmaceutical composition comprises an oral formulation.

Aspect 47A. The pharmaceutical composition of any one of aspects 45A to 46A, wherein the oral formulation comprises an oral suspension.

Aspect 48A. The pharmaceutical composition of any one of aspects 45A to 47A, wherein the pharmaceutical composition comprises an immediate release formulation.

Aspect 49A. The pharmaceutical composition of any one of aspects 45A to 48A, wherein the pharmaceutical composition comprises a controlled release formulation.

Aspect 50A. A method of preparing the granulation of any one of aspects 1A to 44A, comprising: combining the active pharmaceutical ingredient, a binder, and an antistatic agent to form a dry mixture; wet granulating the dry mixture to provide a wet granulation; wet massing the wet granulation to provide a wet massed granulation; and drying the wet massed granulation to provide the granulation.

Aspect 51A. The method of aspect 50A, wherein wet granulating the dry mixture comprises wet granulating for from 5 minutes to 10 minutes.

Aspect 52A. The method of any one of aspects 50A to 51A, wherein wet granulating comprises adding from 5 wt % to 20 wt % total water, wherein wt % is based on the total weight of the active pharmaceutical ingredient.

Aspect 53A. The method of any one of aspects 50A to 52A, wherein during wet granulating the temperature of the wet granulation at a temperature from 20° C. to 25° C.

Aspect 54A. The method of any one of aspects 50A to 53A, wherein wet massing the wet granulation comprises wet massing for from 30 minutes to 60 minutes.

Aspect 55A. The method of any one of aspects 50A to 54A, wherein the method comprises repeating the step of wet granulating and the step of wet massing one or more times before the step of drying.

Aspect 56A. The method of any one of aspects 50A to 55A, wherein the method comprises repeating the step of wet granulating and the step of wet massing one or more times before the step of drying until the specific density of the granulation does not significantly increase.

Aspect 57A. The method of any one of aspects 50A to 56A, wherein wet granulating comprises: granulating the dry mixture for from 5 minutes to 15 minutes at a mixer speed from 800 rpm to 900 rpm and a chopper speed from 3200 rpm to 4000 rpm; adding water at a rate from 0.0025 wt %/min to 0.0075 wt %/min, wherein wt % is based on the total weight of the dry mixture; and maintaining the temperature of the wet granulation during wet granulation at a temperature from 20° C. to 25° C.

Aspect 58A. The method of any one of aspects 50A to 57A, wherein wet granulating comprises: granulating for from 5 minutes to 60 minutes at a mixer speed of 850 rpm and a chopper speed from 3600 rpm; adding water at a rate of 0.005 wt %/min, wherein wt % is based on the total weight of the mixture; and maintaining the temperature of the wet granulation from 20° C. to 25° C.

Aspect 59A. The method of any one of aspects 50A to 58A, wherein wet massing comprises: wet massing for from 30 minutes to 60 minutes at a mixer speed of 550 rpm and a chopper speed from 1,500 rpm to 2,100 rpm; and maintaining the temperature of the wet granulation at a temperature from 15° C. to 25° C.

Aspect 60A. The method of any one of aspects 50A to 58A, wherein wet massing comprises: wet massing for from 30 minutes to 60 minutes at a mixer speed from 500 rpm to 600 rpm and a chopper speed from 1800 rpm; and maintaining the temperature of the wet granulation from 20° C. to 25° C.

Aspect 61A. The method of any one of aspects 50A to 58A, wherein the binder comprises hydroxypropyl cellulose.

Aspect 62A. The method of any one of aspects 50A to 58A, wherein the antistatic agent comprises hydrophilic fumed silica.

Aspect 63A. The method of any one of aspects 50A to 58A, wherein the mixture comprises: greater than 95 wt % of the active pharmaceutical ingredient; greater than 0.25 wt % of a binder; and greater than 0.5 wt % an antistatic agent, wherein wt % is based on the total weight of the mixture.

Aspect 64A. The method of any one of aspects 50A to 58A, wherein the mixture comprises from 98 wt % to 99 wt % of the active pharmaceutical ingredient; from 0.25 wt % to 0.75 wt % of a binder; and from 0.5 wt % to 1.5 wt % of an antistatic agent, wherein wt % is based on the total weight of the mixture.

Aspect 65A. The method of any one of aspects 50A to 58A, wherein the mixture comprises: from 98.2 wt % to 98.8 wt % of the active pharmaceutical ingredient; 0.3 wt % to 0.7 wt % of a binder; and from 0.8 wt % to 1.2 wt % of an antistatic agent, wherein wt % is based on the total weight of the mixture.

Aspect 66A. The method of any one of aspects 50A to 65A, wherein, after drying, the wet granulation comprises from 0.025 wt % to 0.075 wt % water, wherein wt % is based on the total weight of the wet granulation.

Aspect 67A. The method of any one of aspects 50A to 66A, wherein, after drying, the wet granulation comprises 0.05 wt % water, wherein wt % is based on the total weight of the wet granulation.

EXAMPLES

Embodiments provided by the present disclosure are further illustrated by reference to the following examples, which describe the granulations, granules, oral dosage formulations, and methods of making the granulations provided by the present disclosure. It will be apparent to those skilled in the art that many modifications, both to materials, and methods, may be practiced without departing from the scope of the disclosure.

In the examples the following materials were used. The active pharmaceutical ingredient was the compound of Formula (2a), 4-((L-valyl)oxy)butanoic acid. The binder was Pharmacoat® 606 HPMC (hydroxypropylmethyl cellulose) (Shin-Etsu Chemical Company, Ltd.) (Example 1) or Klucel® EXF HPC (hydroxypropylcellulose) (Ashland) (Example 2-9). The antistatic agent was Aerosil® 200 (hydrophilic fumed silica, BWT SA 200 m²/g) (Evonik Industries). Milling was done using a Comil® (Quadro Engineering).

The constituents of the dry mixture for each of the examples is provided in Table 1.

TABLE 1

Dry mixture constituents.

| Example | Dry Mixture (wt %) | | |
|---|---|---|---|
| | API | Binder | Antistatic Agent |
| 1 | 96.0 | 3.0 | 1.0 |
| 2 | 98.6 | 0.4 | 1.0 |
| 3 | 98.5 | 0.5 | 1.0 |
| 4 | 98.0 | 1.0 | 1.0 |
| 5 | 98.5 | 0.5 | 1.0 |
| 6 | 98.5 | 0.5 | 1.0 |
| 7 | 98.5 | 0.5 | 1.0 |
| 8 | 98.5 | 0.5 | 1.0 |
| 9 | 98.5 | 0.5 | 1.0 |

The process conditions for each of Examples 1-9 is summarized in FIG. 11 and the properties of the granulations are summarized in FIG. 12.

Example 1

Pharmaceutical Granulation (1)

The constituents of the dry mixture in terms of wt % are provided in Table 1.

A total of 3.76 wt % water was added during wet granulation, where wt % is based on the total weight of the dry mixture. Water was added until the bed height decreased approximately two-fold signifying a substantial increase in bulk density. The wet granulation was granulated for 7 minutes at a mixer speed of 800 rpm and a chopper speed of 2,000 rpm, with an average temperature of the wet granulation of 25.2° C.

The wet granulation was wet massed for 30 minutes.

Certain properties of pharmaceutical granulation (1) are shown in FIG. 12.

Figure 1B:
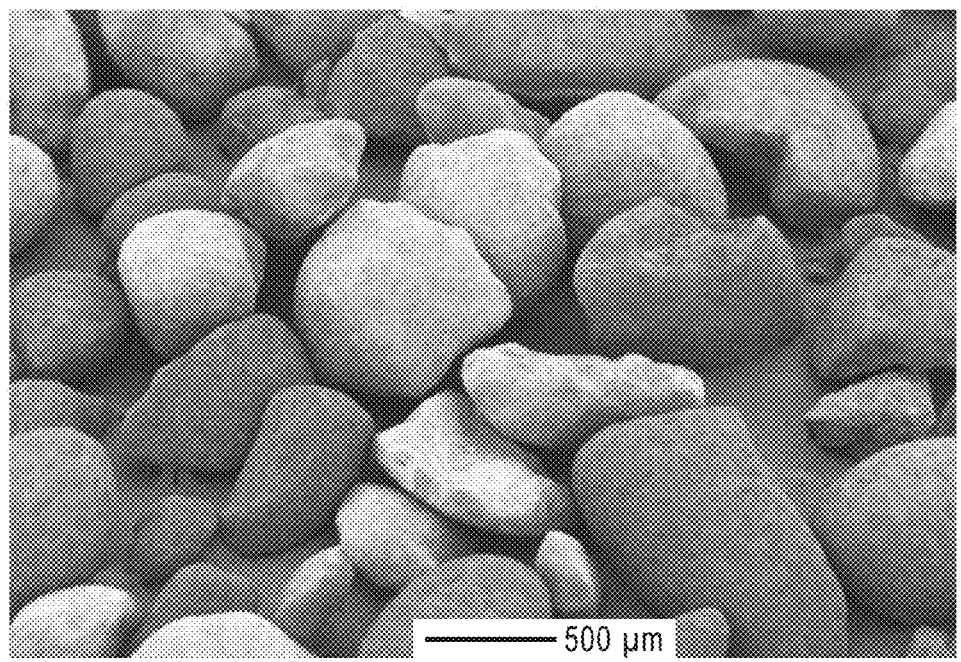
FIGS. 1B and 1C show SEM images of pharmaceutical granulation (1) at two different magnifications.
Figure 1C:
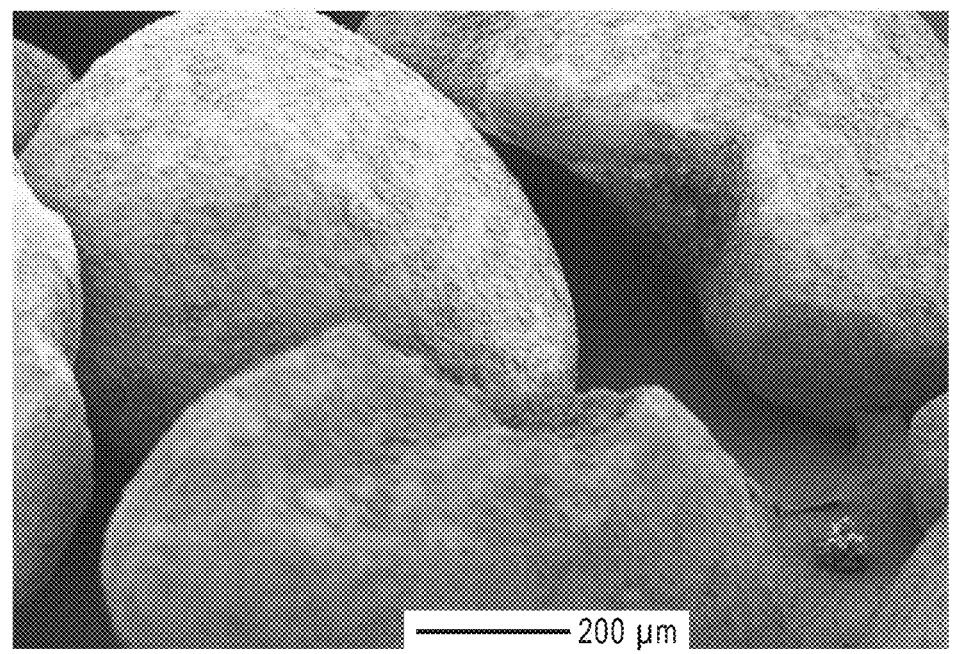

The granule size distribution during wet massing is shown in FIG. 1A and SEM images of the resulting granules are shown in FIGS. 1B and 1C at magnifications of 34× and 100×, respectively.

Example 2

Pharmaceutical Granulation (2)

The constituents of the dry mixture in terms of wt % are provided in Table 1.

A total of 3.69 wt % water was added during wet granulation, where wt % is based on the total weight of the dry mixture. The wet granulation was granulated for 6 minutes at a mixer speed of 800 rpm and a chopper speed of 2,000 rpm, with an average temperature of the wet granulation of 25.4° C.

The wet granulation was wet massed for 45 minutes at a mixer speed of 1,200 rpm and a chopper speed of 2,000 rpm, while the temperature of the wet granulation was maintained at an average temperature of 32.1° C.

Certain properties of pharmaceutical granulation (2) are shown in FIG. 12.

Figure 2A:
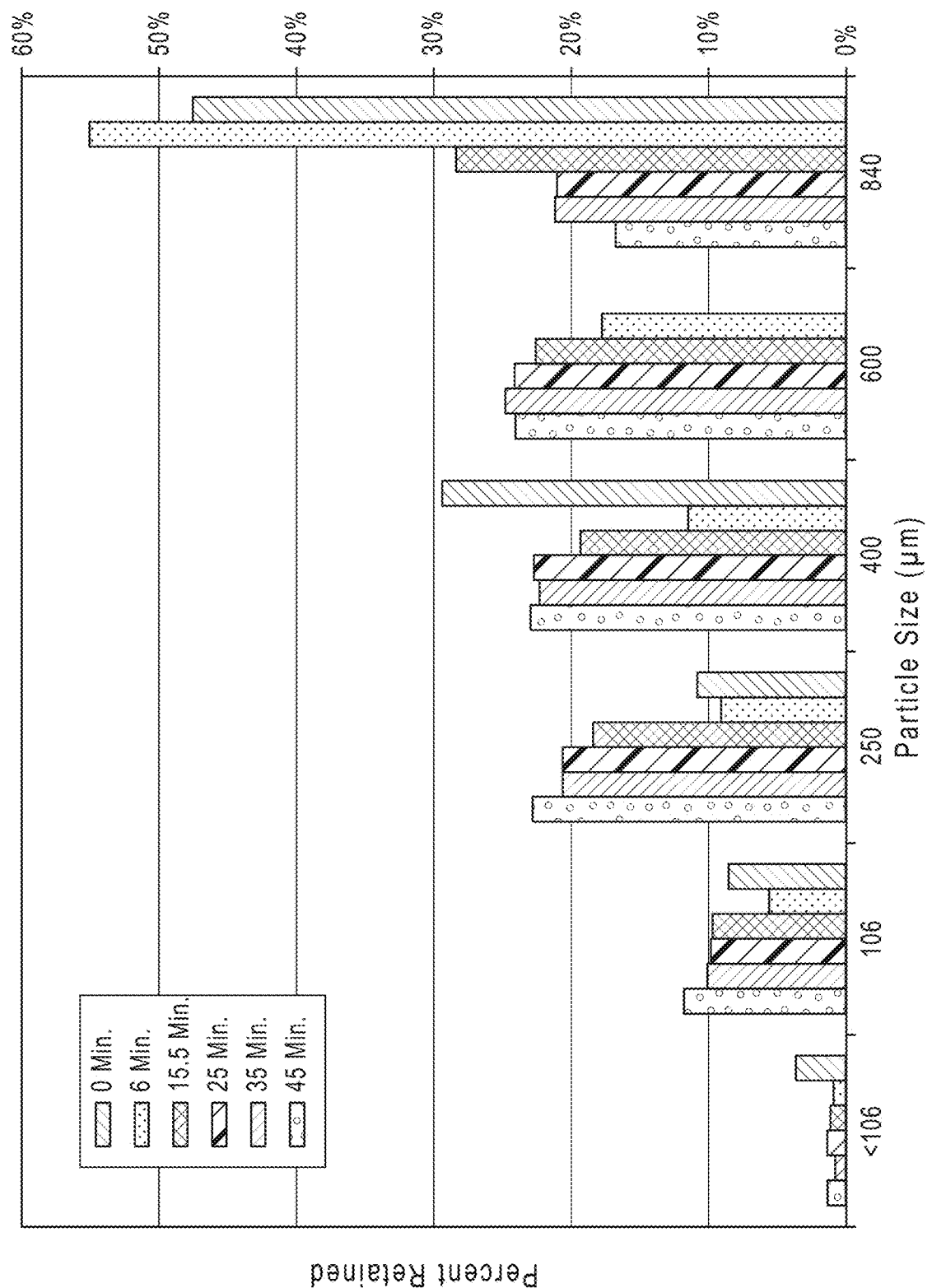
FIG. 2A shows the particle size distribution for pharmaceutical granulation (2) prepared using different wet massing times.
Figure 2B:
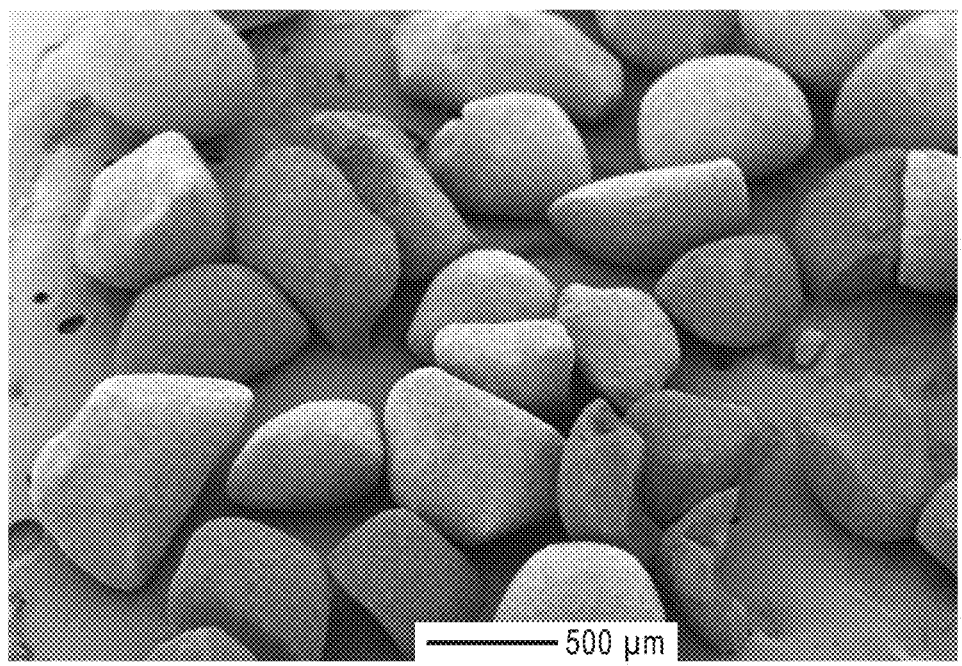
FIGS. 2B and 2C show SEM images of pharmaceutical granulation (2) at two different magnifications.
Figure 2C:
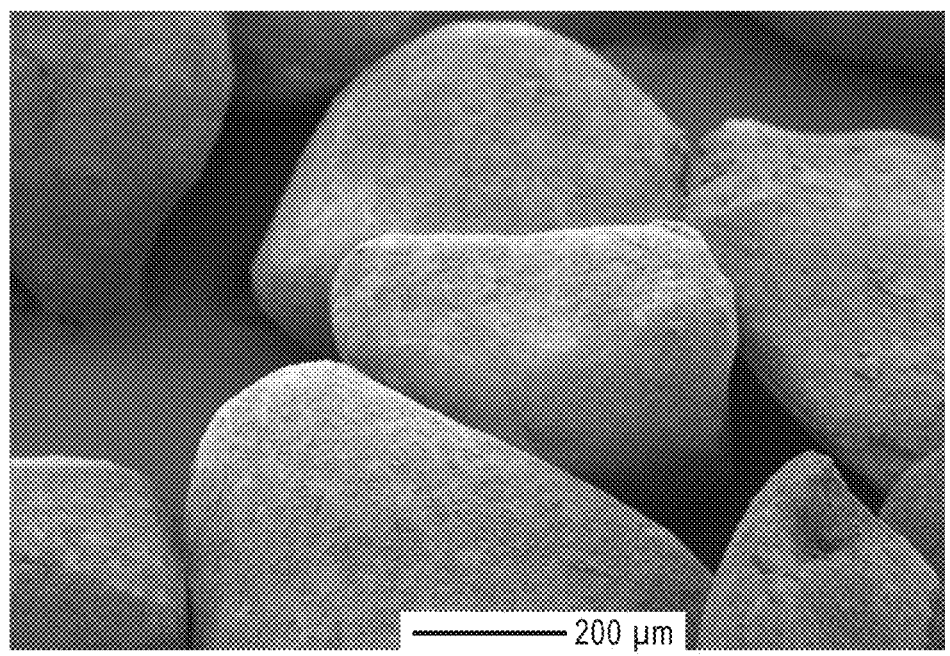

The granule size distribution during wet massing is shown in FIG. 2A and SEM images of the resulting granules are shown in FIGS. 2B and 2C at magnifications of 34× and 100×, respectively.

Example 3

Pharmaceutical Granulation (3)

The constituents of the dry mixture in terms of wt % are provided in Table 1.

A total of 3.75 wt % water was added during wet granulation, where wt % is based on the total weight of the dry mixture. The wet granulation was granulated for 6 minutes at a mixer speed of 850 rpm and a chopper speed of 3,600 rpm, with an average temperature of the wet granulation of 32° C.

After initial granulation, sub-batches were combined into a jacketed bowl for wet massing. After 20 minutes of wet massing, there was no visible change to the granulation.

Wet granulation was continued for an additional 24 minutes at a mixer speed of 850 RPM and a chopper speed of 3,600 rpm. An additional amount of 8.0 wt % water added during wet granulation, where wt % is based on the total weight of the dry mixture.

The wet granulation was wet massed for 36 minutes at a mixer speed of 850 rpm and a chopper speed of 3,600 rpm, while the temperature of the wet granulation was between 16° C. and 33° C. Wet granulation was continued for an additional 24 minutes at a mixer speed of 850 rpm and a chopper speed of 3,600 rpm. An additional amount of 8.0 wt % water was added during wet granulation, where wt % is based on the total weight of the dry mixture.

Certain properties of pharmaceutical granulation (3) are shown in FIG. 12.

Figure 3A:
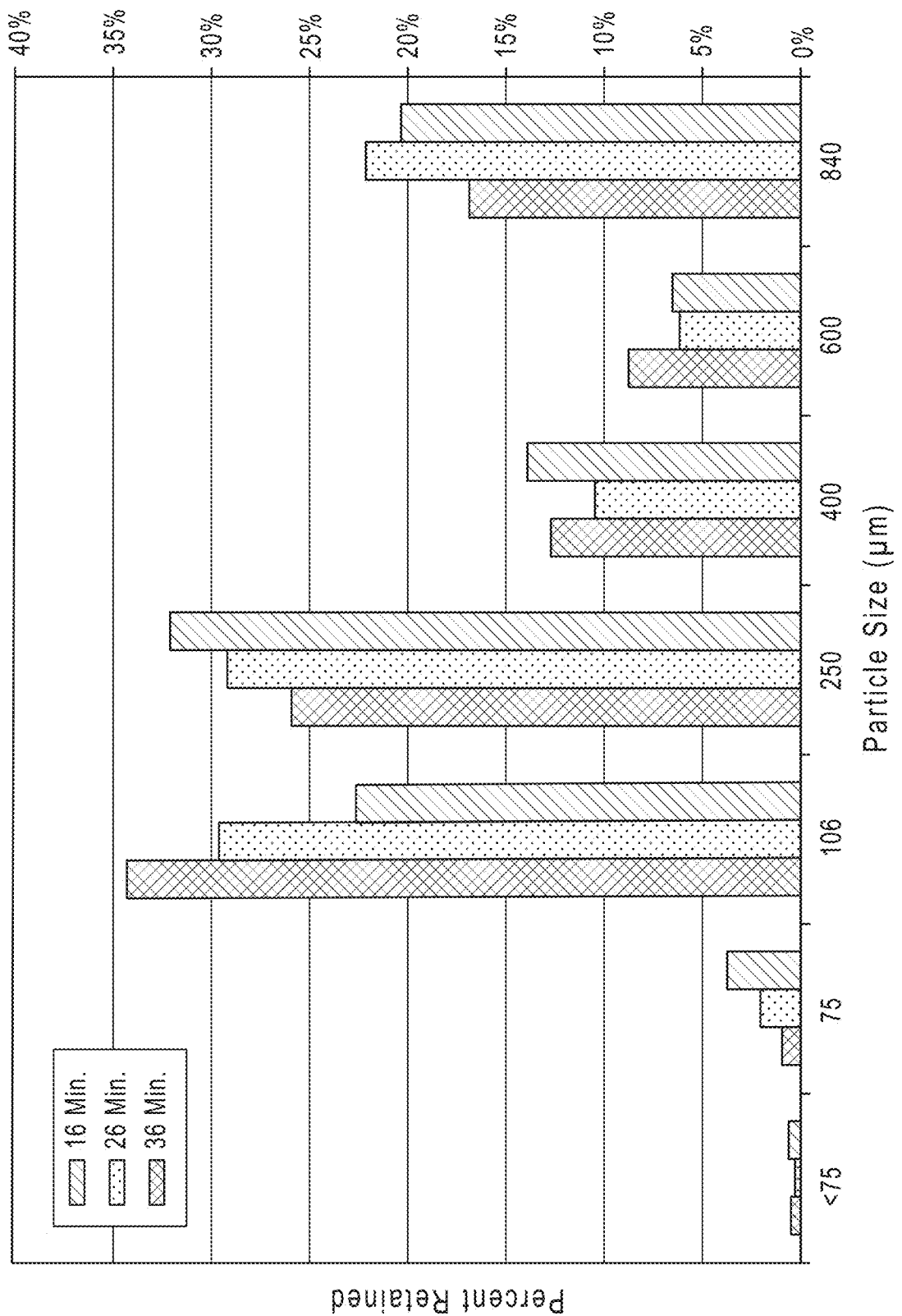
FIG. 3A shows the particle size distribution for pharmaceutical granulation (3) prepared using different wet massing times.
Figure 3B:
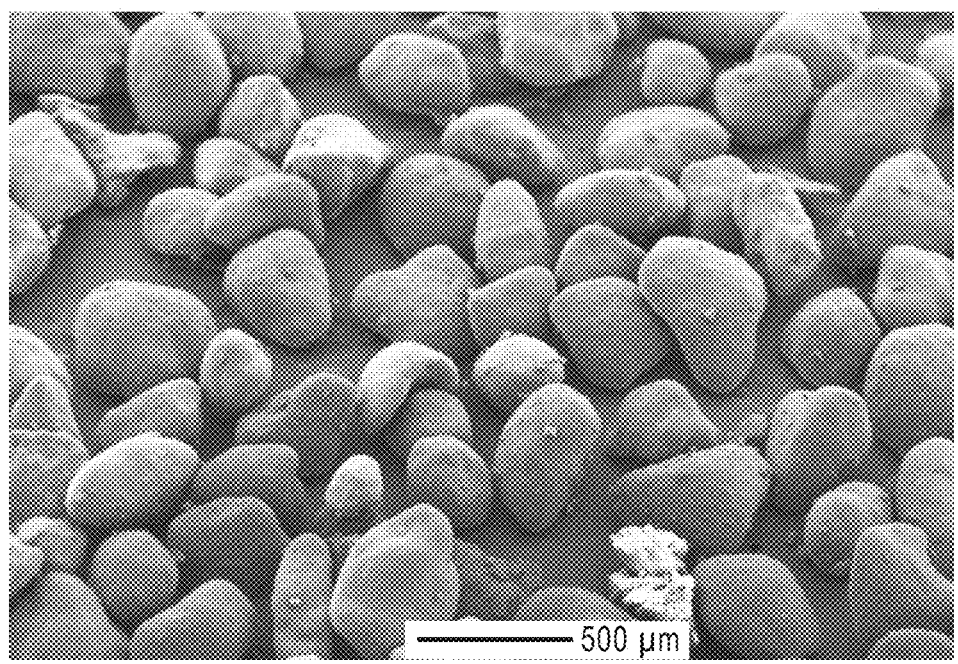
FIGS. 3B and 3C show SEM images of pharmaceutical granulation (3) at two different magnifications.
Figure 3C:
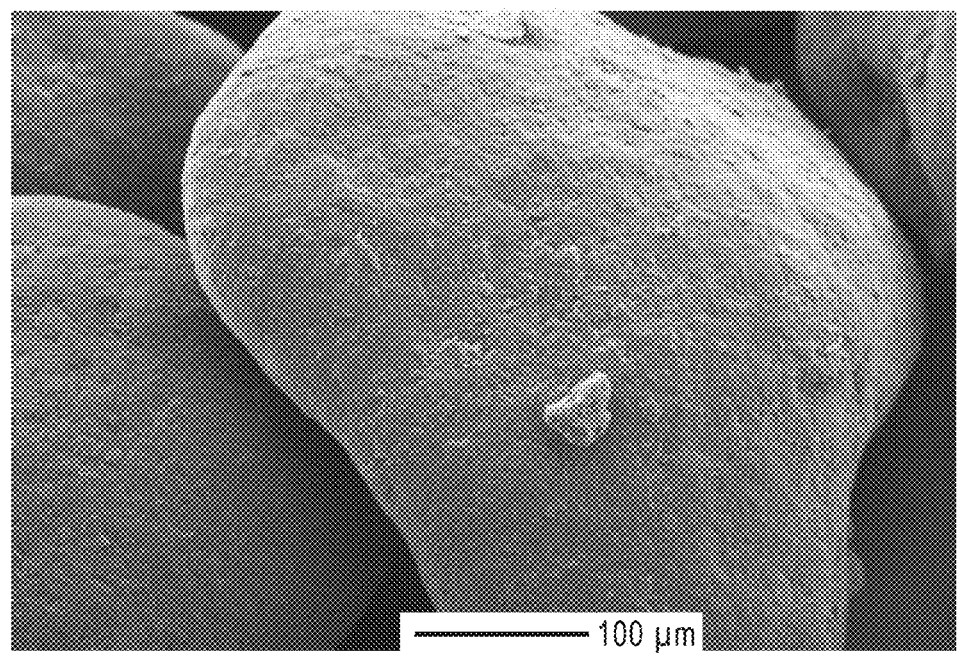

The granule size distribution during wet massing is shown in FIG. 3A and SEM images of the resulting granules are shown in FIGS. 3B and 3C at magnifications of 40× and 220×, respectively.

Example 4

Pharmaceutical Granulation (4)

The constituents of the dry mixture in terms of wt % are provided in Table 1. The active pharmaceutical ingredient was passed through a Comil® fitted with a 0.045-inch screen before adding to the dry mixture. The active pharmaceutical ingredient was not jet milled.

A total of 5.0 wt % water was added during wet granulation, where wt % is based on the total weight of the dry mixture. Water was added using a syringe and a 2-fluid spray nozzle with atomizing air set to 4 psi. The wet granulation was granulated for 10 minutes at a mixer speed of 850 rpm and a chopper speed of 3,600 rpm.

A jacketed 4 L bowl was used throughout processing. During wet massing, an attached chiller was used to prevent overheating of the product. After initial granulation, sub-batches were combined into the jacketed bowl for additional granulation followed by wet massing.

Wet granulation was continued for an additional 14 min. An additional 5.1 wt % water was added during this second phase of the granulation, where wt % is based on the total weight of the dry mixture.

The wet granulation was wet massed for 50 minutes at a mixer speed of 850 rpm and a chopper speed of 3,600 rpm, while the temperature of the wet granulation was maintained between 22.9° C. and 25.4° C.

Certain properties of pharmaceutical granulation (4) are shown in FIG. 12.

Figure 4B:
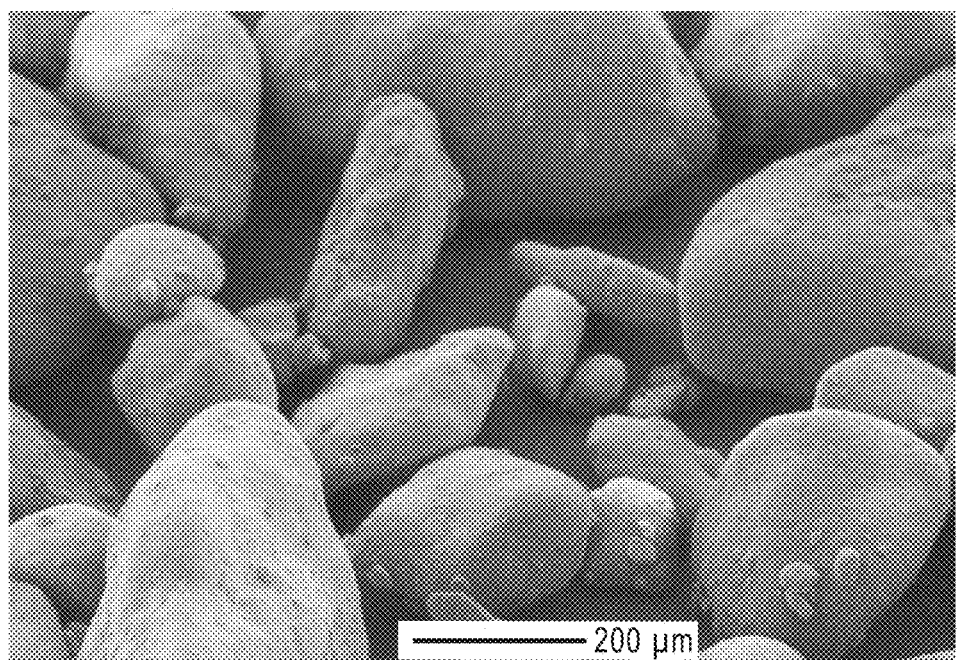
FIGS. 4B and 4C show SEM images of pharmaceutical granulation (4) at two different magnifications.
Figure 4C:
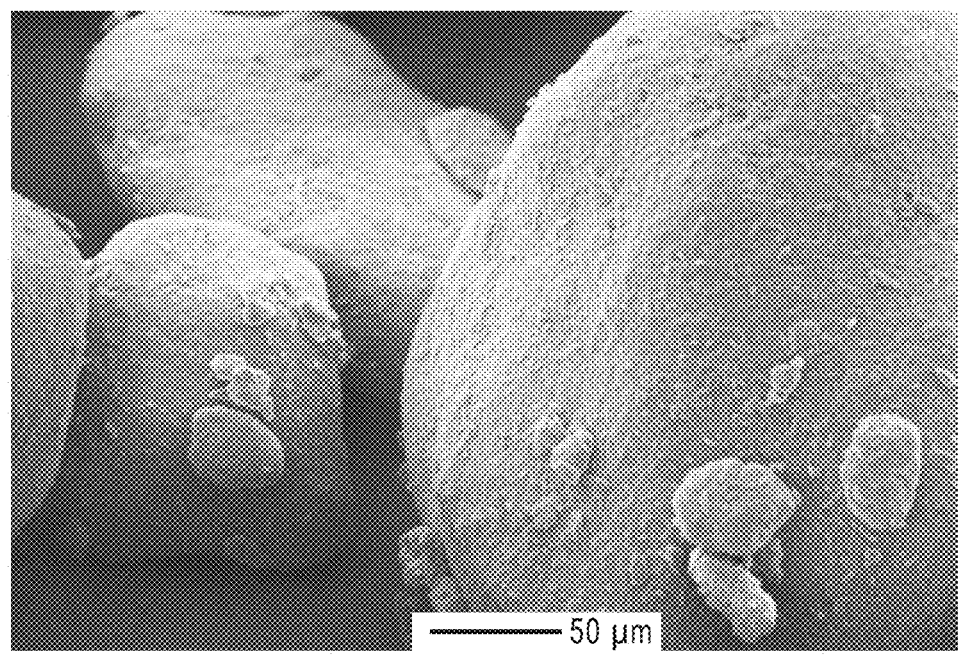

The granule size distribution before and after wet massing for 20 minutes is shown in FIG. 4A and SEM images of the resulting granules are shown in FIGS. 4B and 4C at magnifications of 110× and 340×, respectively.

Example 5

Pharmaceutical Granulation (5)

The constituents of the dry mixture in terms of wt % are provided in Table 1. The active pharmaceutical ingredient was passed through a Comil® fitted with a 0.045-inch screen before adding to the dry mixture. The active pharmaceutical ingredient was not jet milled.

A total of 5.0 wt % water was added during wet granulation, where wt % is based on the total weight of the dry mixture. Water was added using a syringe and a 2-fluid spray nozzle with atomizing air set to 4 psi. The wet granulation was granulated for 10 minutes at a mixer speed of 850 rpm and a chopper speed of 3,600 rpm.

After initial granulation, sub-batches were combined into a jacketed bowl for the first wet massing. The initial granulation was wet massed for 20 min at a mixer speed of 850 rpm and a chopper speed of 3,600 rpm. During wet massing the temperature was maintained between 21° C. and 22° C. using a water chiller attached to a jacketed 4 L bowl.

After wet massing, a second wet granulation was performed. During the second wet granulation, an additional amount of 6.5 wt % water was added at a mixer speed of 547 rpm and a chopper speed of 1800 rpm.

After the second wet granulation, a second wet massing was performed. The second wet granulation was wet massed for an additional 40 min at a mixer speed of 547 rpm and a chopper speed of 3600 rpm. The bowl temperature was maintained between 24° C. and 31° C.

Certain properties of pharmaceutical granulation (5) are shown in FIG. 12.

Figure 5A:
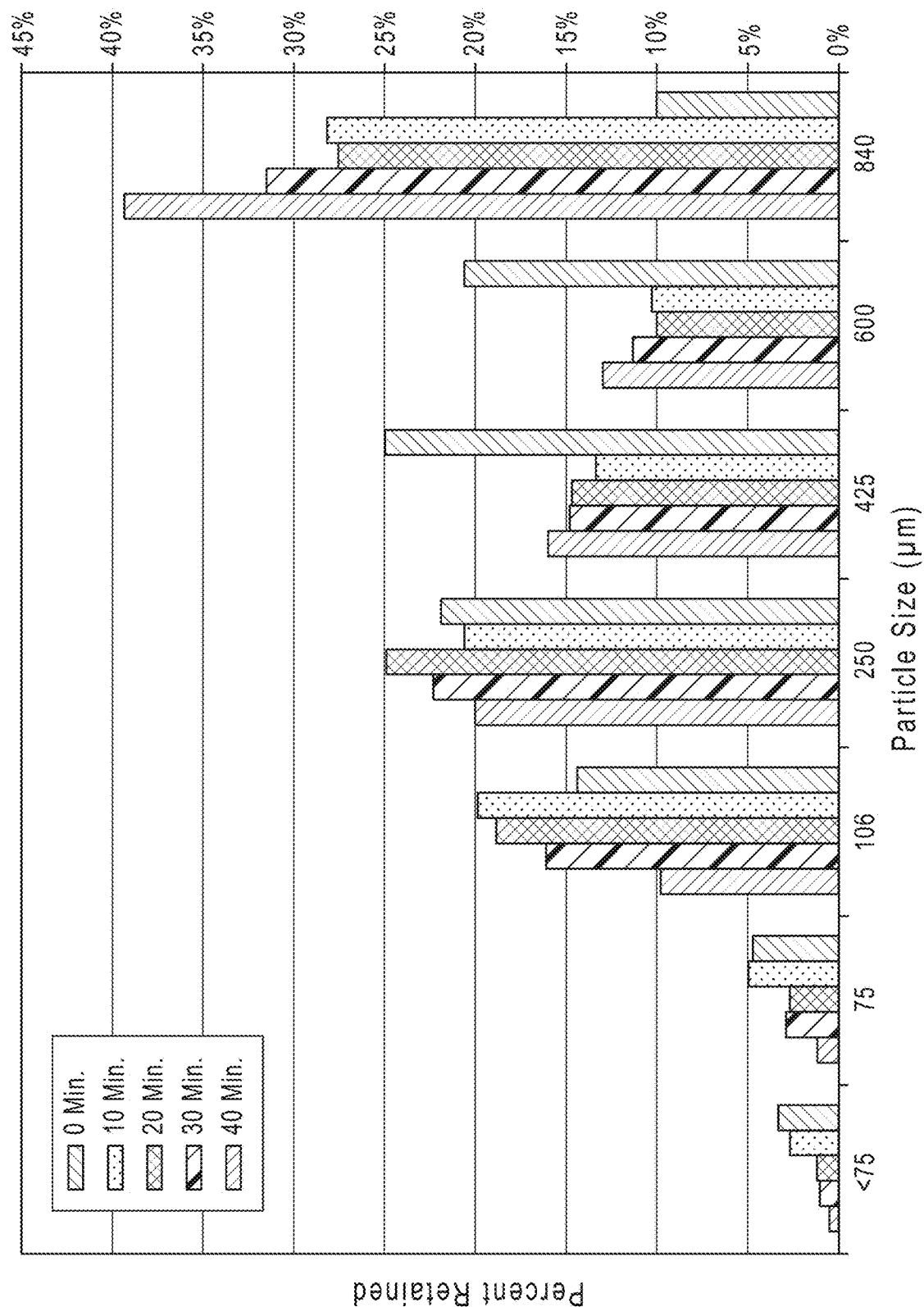
FIG. 5A shows the particle size distribution for pharmaceutical granulation (5) prepared using different wet massing times.
Figure 5B:
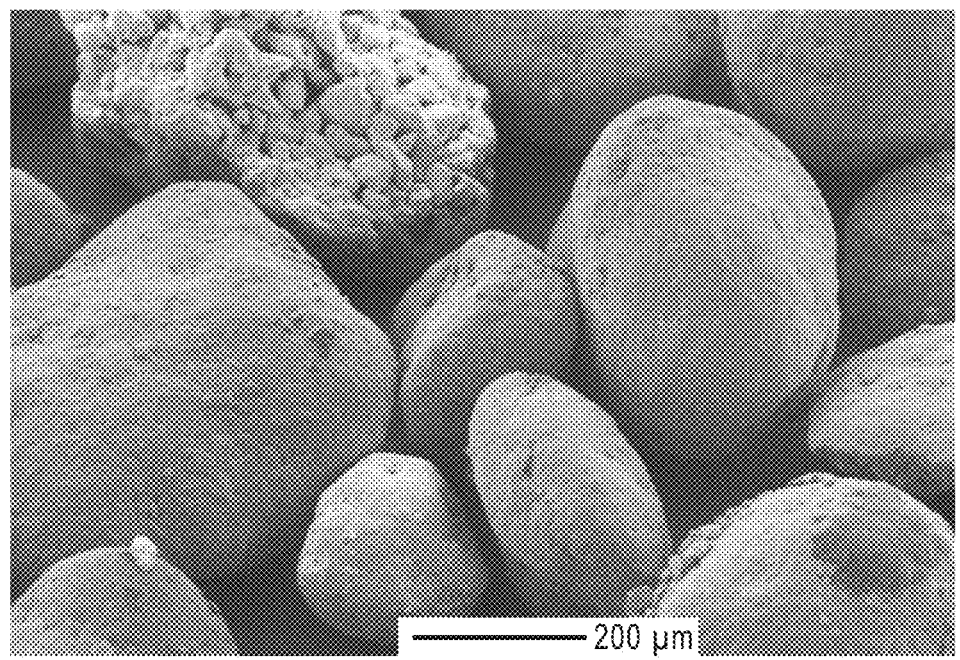
FIGS. 5B and 5C show SEM images of pharmaceutical granulation (5) at two different magnifications.
Figure 5C:
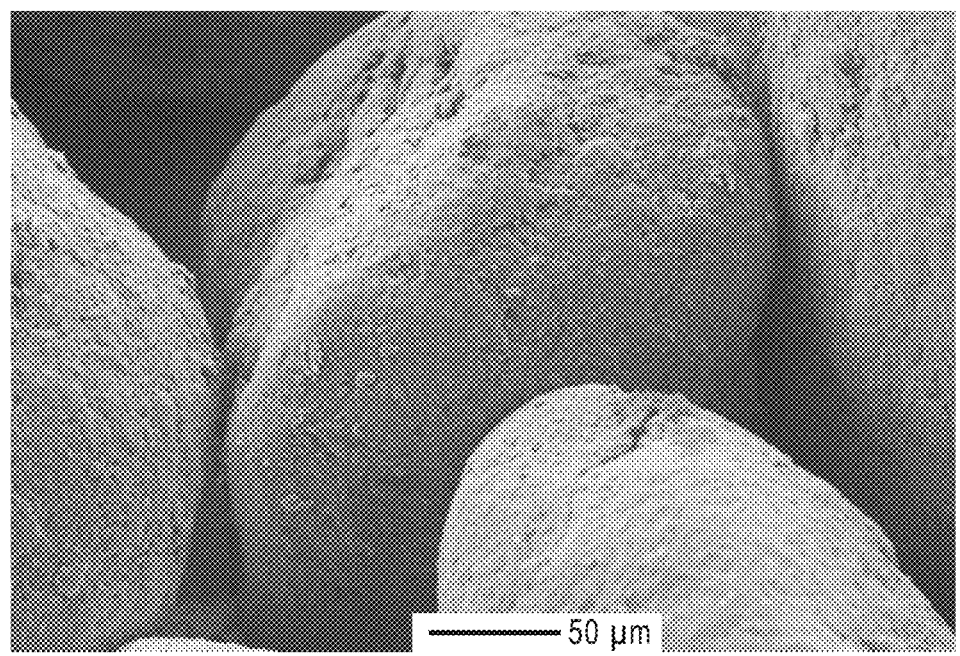

The granule size distribution during wet massing is shown in FIG. 5A and SEM images of the resulting granules are shown in FIGS. 5B and 5C at magnifications of 110× and 340×, respectively.

Example 6

Pharmaceutical Granulation (6)

The constituents of the dry mixture in terms of wt % are provided in Table 1. The active pharmaceutical ingredient was passed through a Comil® fitted with a 0.045-inch screen before adding to the dry mixture. The active pharmaceutical ingredient was not jet milled.

A total of 5.0 wt % water was added during wet granulation, where wt % is based on the total weight of the dry mixture. Water was added using a syringe and a 2-fluid spray nozzle with atomizing air set to 4 psi. The wet granulation was granulated for 10 min at a mixer speed of 850 rpm and a chopper speed of 3,600 rpm.

After the initial granulation, the two sub-batches were combined into the jacketed bowl for the first wet massing. The initial granulation was wet massed for 20 min at a mixer speed of 547 rpm and a chopper speed of 1,800 rpm. During wet massing the temperature was maintained between 21° C. and 22° C. using a water chiller attached to a jacketed 4 L bowl.

After wet massing, a second wet granulation was performed. During the second wet granulation, an additional amount of 3.0 wt % water was added at a mixer speed of 850 rpm and a chopper speed of 3600 rpm.

After the second wet granulation, a second wet massing was performed. The second wet granulation was wet massed for an additional 30 min at a mixer speed of 547 rpm and a chopper speed of 3600 rpm. During the second wet massing the bowl temperature was maintained between 18° C. and 21° C.

Certain properties of pharmaceutical granulation (6) are shown in FIG. 12.

Figure 6A:
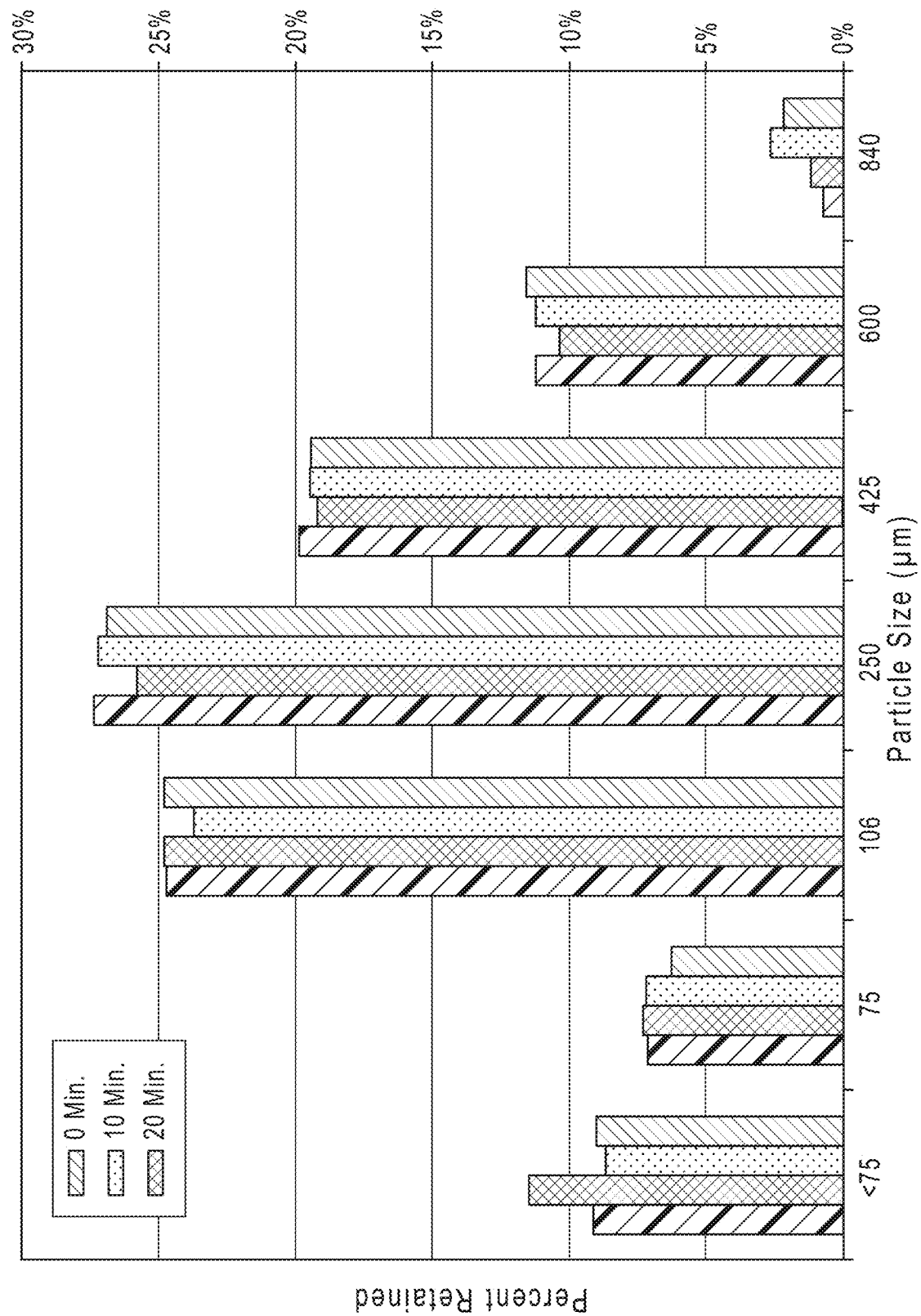
FIG. 6A shows the particle size distribution for pharmaceutical granulation (6) prepared using different wet massing times.
Figure 6B:
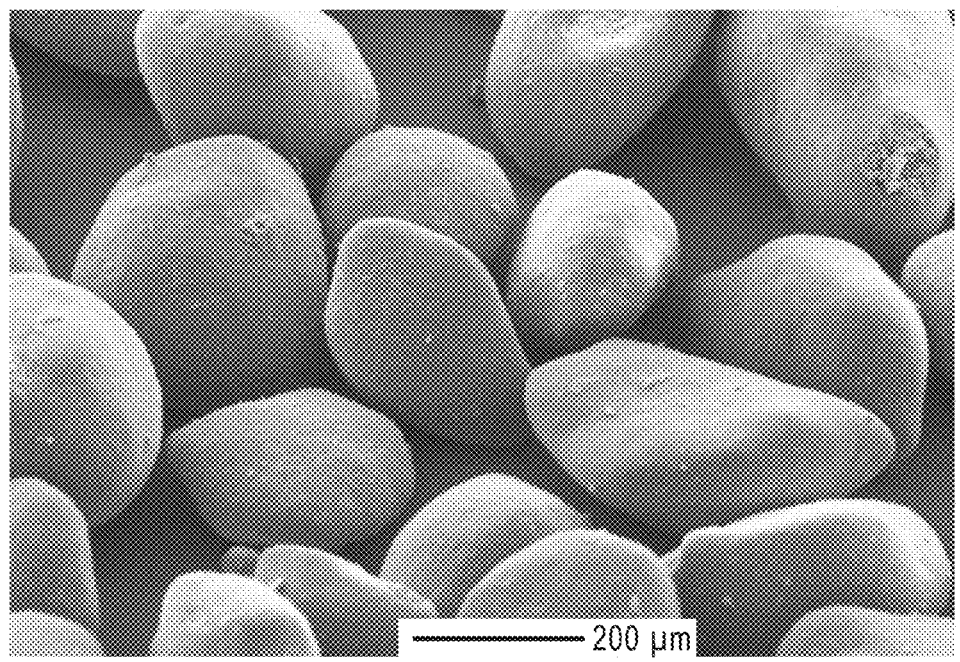
FIGS. 6B and 6C show SEM images of pharmaceutical granulation (6) at two different magnifications.
Figure 6C:
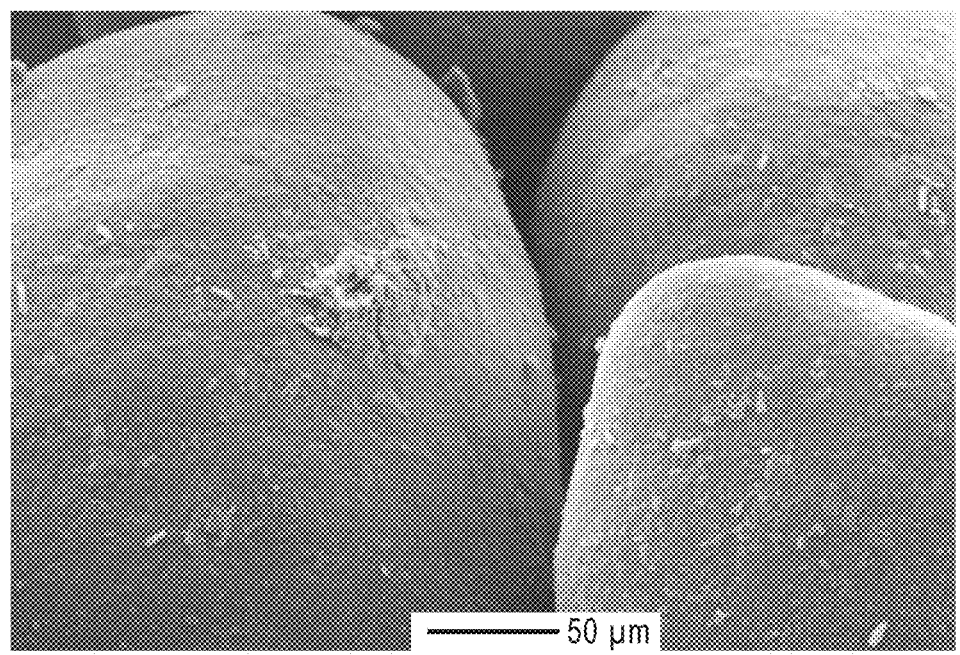

The granule size distribution during wet massing is shown in FIG. 6A and SEM images of the resulting granules are shown in FIGS. 6B and 6C at magnifications of 110× and 340×, respectively.

Example 7

Pharmaceutical Granulation (7)

The constituents of the dry mixture in terms of wt % are provided in Table 1. A different lot of active pharmaceutical ingredient was used for this granulation. The active pharmaceutical ingredient was less agglomerated than the active pharmaceutical ingredient used in Examples 1-6. The active pharmaceutical ingredient was passed through a Comil® fitted with a 0.045-inch screen before adding to the dry mixture. The active pharmaceutical ingredient was not wet milled.

A total of 5.0 wt % water was added during wet granulation, where wt % is based on the total weight of the dry mixture. Water was added using a syringe and a 2-fluid spray nozzle with atomizing air set to 4 psi. The wet granulation was granulated for 9.7 minutes at a mixer speed of 850 rpm and a chopper speed of 3,600 rpm.

The wet granulation was wet massed for up to 20 minutes at a mixer speed of 547 rpm and a chopper speed of 1,800 rpm, while the temperature was maintained at 21° C.

Certain properties of pharmaceutical granulation (7) are shown in FIG. 12.

Figure 7B:
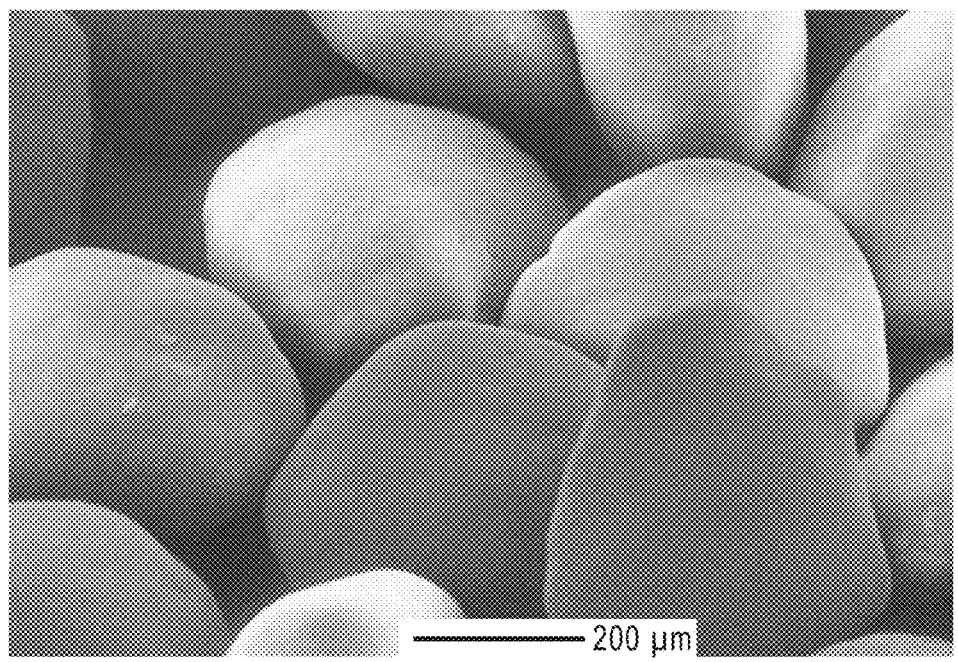
FIGS. 7B and 7C show SEM images of pharmaceutical granulation (7) at two different magnifications.
Figure 7C:
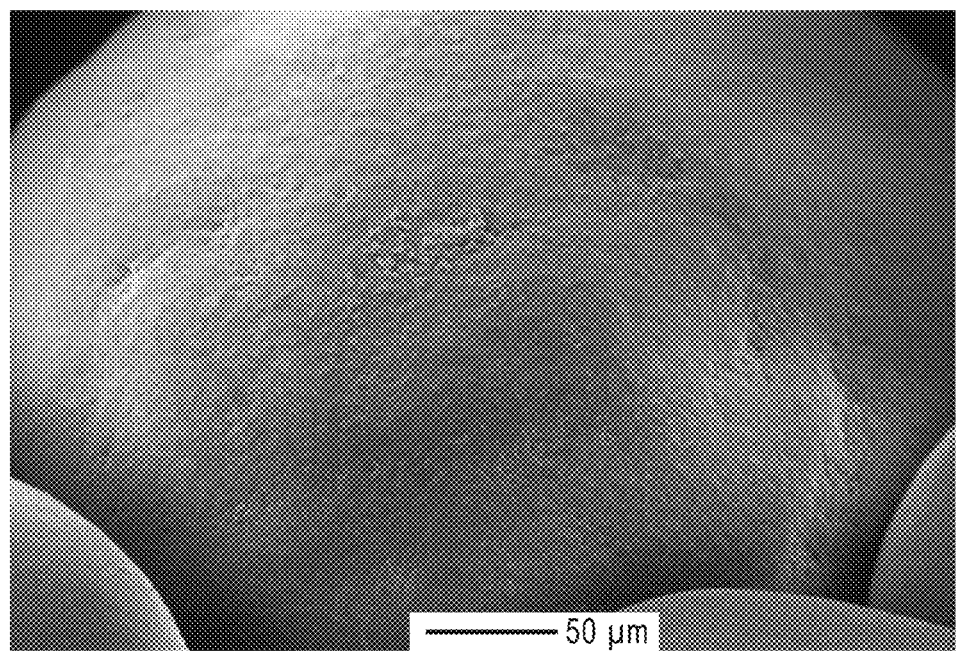

The granule size distribution during wet massing is shown in FIG. 7A and SEM images of the resulting granules are shown in FIGS. 7B and 7C at magnifications of 110× and 340×, respectively.

Example 8

Pharmaceutical Granulation (8)

The constituents of the dry mixture in terms of wt % are provided in Table 1. The active pharmaceutical ingredient used in Example 8 was the same as that used in Examples 7 and 9.

A total of 4.8 wt % water was added during wet granulation, where wt % is based on the total weight of the dry mixture. Water was added using a syringe and a 2-fluid spray nozzle with atomizing air set to 4 psi. The wet granulation was granulated for 11.5 minutes at a mixer speed of 850 rpm and a chopper speed of 3,600 rpm.

The wet granulation was wet massed for up to 60 minutes at a mixer speed of 547 rpm and a chopper speed of 1,800 rpm, while the temperature of the wet granulation was between 21° C. and 23.5° C.

Certain properties of pharmaceutical granulation (8) are shown in FIG. 12.

Figure 8A:
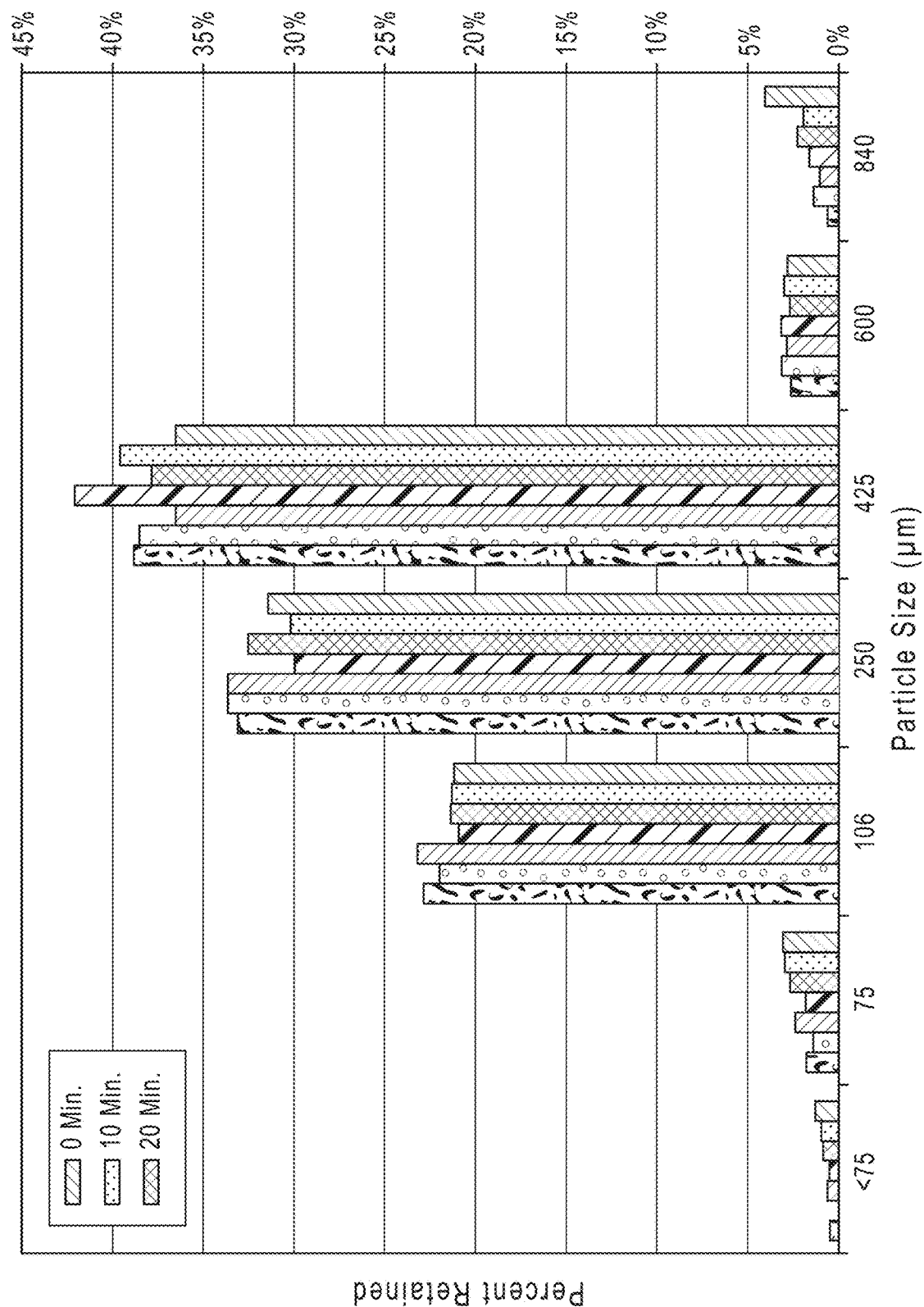
FIG. 8A shows the particle size distribution for pharmaceutical granulation (8) prepared using different wet massing times.
Figure 8B:
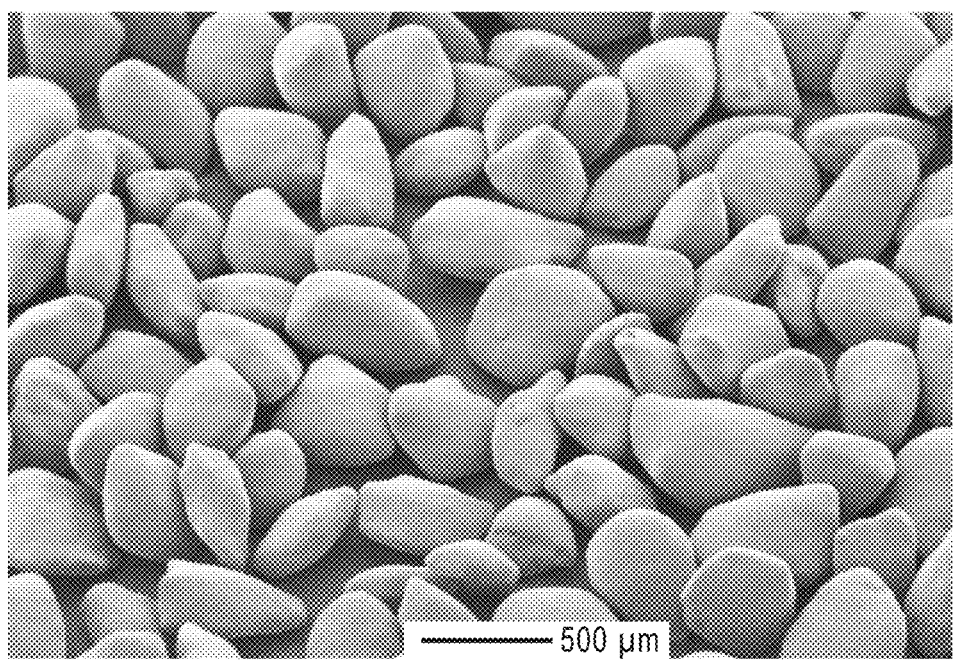
FIGS. 8B and 8C show SEM images of pharmaceutical granulation (8) at two different magnifications.
Figure 8C:
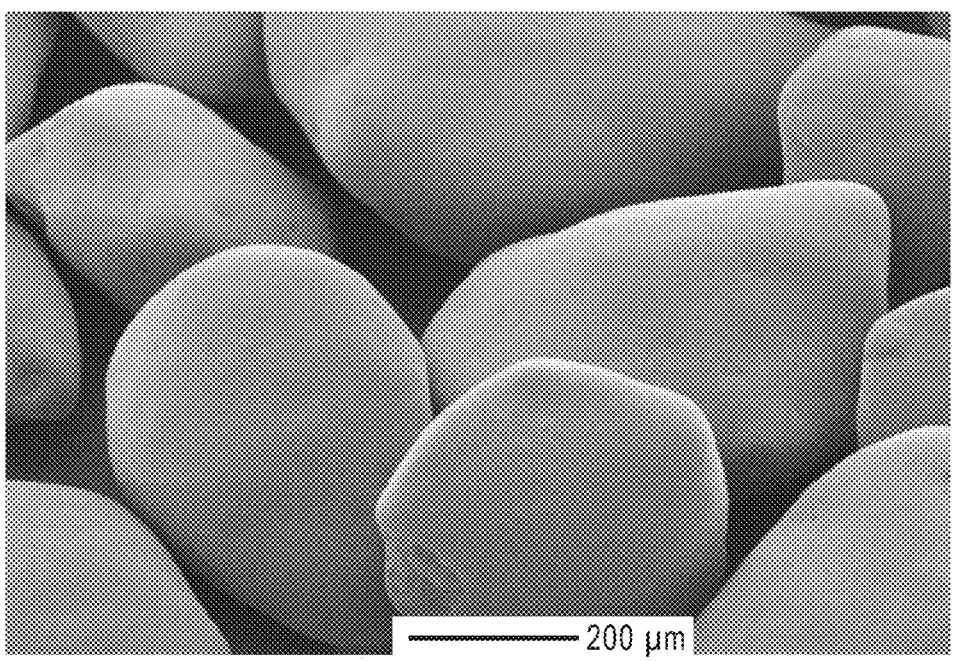

The granule size distribution during wet massing is shown in FIG. 8A and SEM images of the resulting granules are shown in FIGS. 8B and 8C at magnifications of 34× and 110×, respectively.

Example 9

Pharmaceutical Granulation (9)

An active pharmaceutical ingredient having a bulk density of 0.263 g/mL was passed through a Comil® fitted with a 0.056-inch screen. Prior to co-milling the active pharmaceutical ingredient was stored in a dry environment.

The constituents of the dry mixture in terms of wt % are provided in Table 1.

Distilled water (4.7 wt %) was added to the dry mixture using a pump and a 2-fluid spray nozzle with atomizing air set to 4 psi.

The granulation was retained in a jacketed 4-liter bowl throughout processing.

The wet granulation was granulated for 9.7 minutes at a mixer speed of 850 rpm and a chopper speed of 3,600 rpm.

The wet granulation was wet massed for up to 60 minutes at a mixer speed of 547 rpm and a chopper speed of 1,800 rpm, while the temperature of the wet granulation was between 23.1° C. and 23.6° C. During wet massing a chiller was attached to the bowl to maintain the temperature less than 25° C.

The conditions during wet massing are shown in Table 2.

TABLE 2

Wet massing conditions.

| Time (min) | Power (kW) | Bowl Temperature (° C.) | Bath Temperature (° C.) | Bed Height (cm) | Mixer/Chopper (rpm) |
|---|---|---|---|---|---|
| 10 | 0.44 | — | 21.0 | 4.0 | 547/1800 |
| 20 | 0.40 | 23.1 | 21.0 | 4.0 | |
| 40 | 0.43 | 23.2 | 21.0 | 3.5 | |
| 60 | 0.40 | 23.6 | 21.0 | 3.5 | |

The evolution of the PSD during wet massing is shown in FIG. 9A. The number of fines and large particles continued to decrease during wet massing.

A more detailed PSD of the granulation after wet massing for 60 minutes as determined using laser diffraction is shown in FIG. 9F.

SEM images of the granules are shown in FIGS. 9B to 9E at magnifications of 110×, 220×, 1,000×, and 2,000×, respectively.

Example 10

Active Pharmaceutical Ingredient Characterization

Figure 10A:
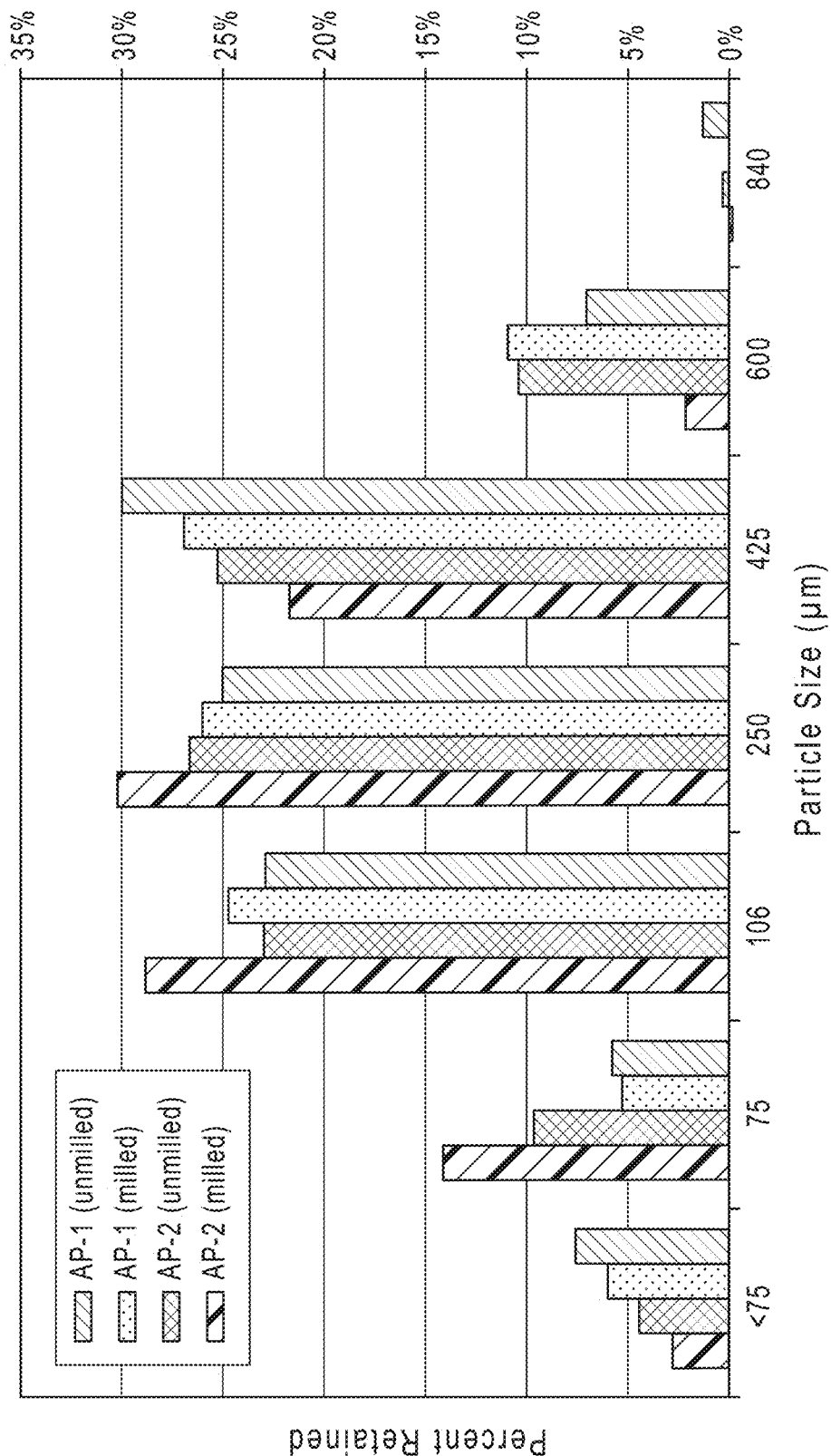
FIGS. 10A and 10B show active pharmaceutical ingredient particle size distributions before and after jet milling.
Figure 10B:
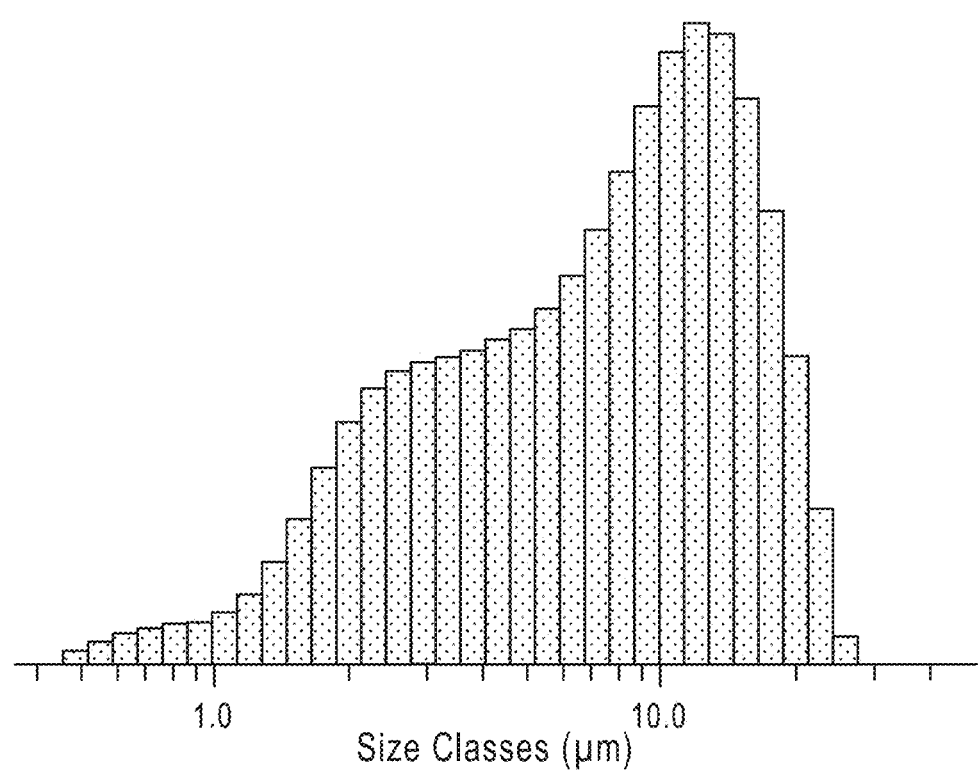

FIGS. 10A and 10B show the particle size distribution of granules prepared from un-milled active pharmaceutical ingredient and from milled active pharmaceutical ingredient, respectively. This active pharmaceutical ingredient was the same as was used in Examples 7-9 and had a purity of 99.3%.

The active pharmaceutical ingredient used in Examples 1-6 had a bulk density of 0.15 g/mL.

The active pharmaceutical ingredient used in Examples 12 and 13 had a different morphology generally characterized by a larger crystal size (FIGS. 13-18). The as-crystallized active pharmaceutical ingredient was jet-milled to reduce the crystal size to less than about 20 µm.

Figure 13:
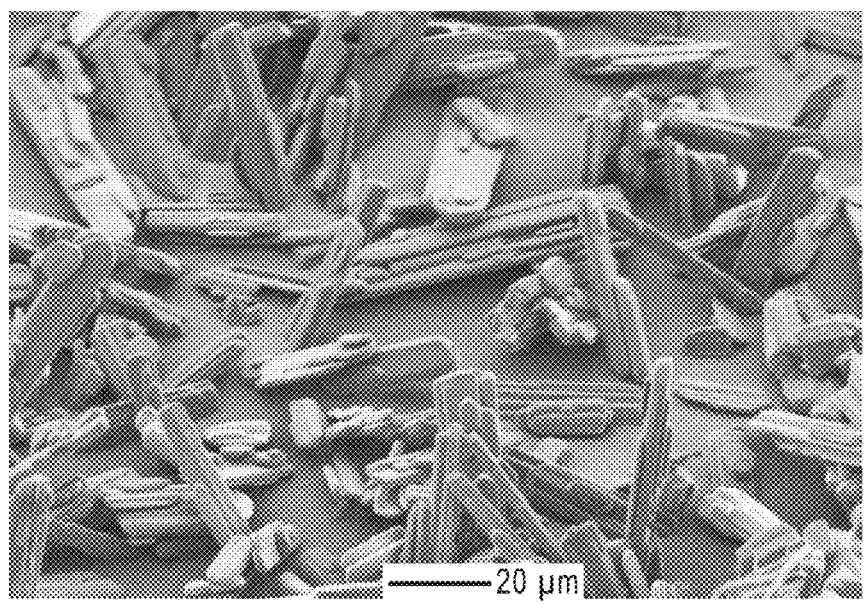
FIG. 13 shows an SEM image of the as-crystallized active pharmaceutical ingredient of Example 13 at 700× magnification.

FIG. 13 shows an SEM image of as-crystallized active pharmaceutical ingredient at 700× magnification.

Figure 14:
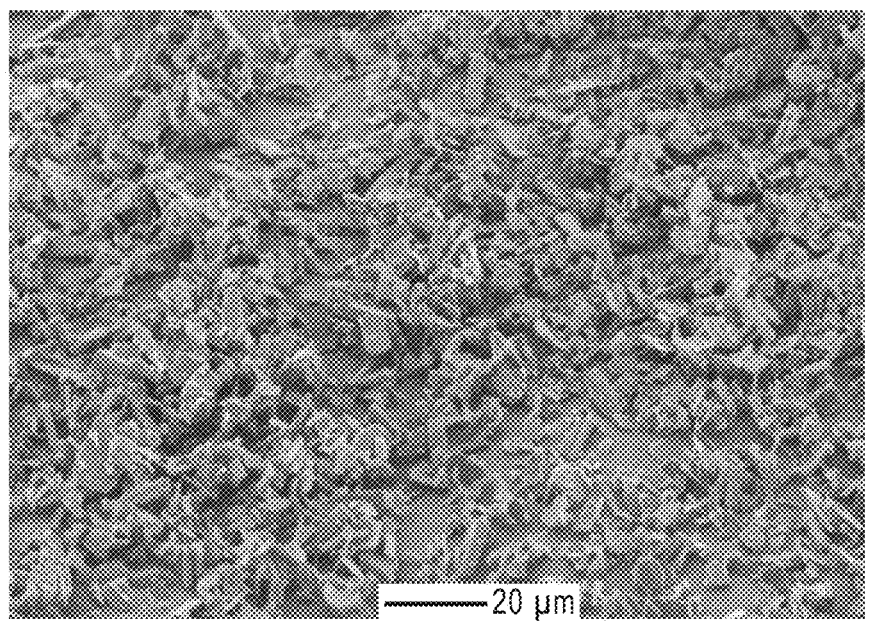
FIG. 14 shows an SEM image of the active pharmaceutical ingredient of Example 13 at 700× magnification after jet-milling.

FIG. 14 shows an SEM image of jet-milled active pharmaceutical ingredient at 700× magnification.

Figure 15:
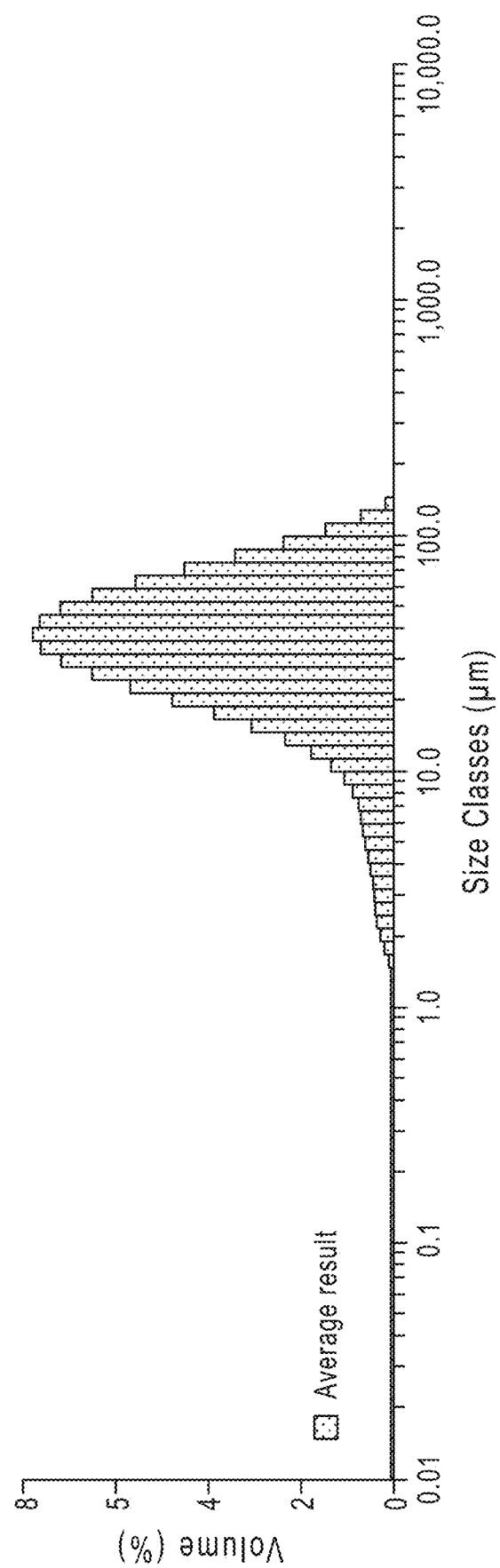
FIG. 15 shows the particle size distribution of the as-crystallized active pharmaceutical ingredient described in Example 13.

FIGS. 15 and 16 show a particle size distribution of as-crystallized active pharmaceutical ingredient and jet-milled active pharmaceutical ingredient, respectively, as determined by laser diffraction. The PSD of the as-crystallized active pharmaceutical ingredient was characterized by a D10 of 11.8 μm, a D50 of 34.0 μm, and a D90 of 72.3 μm. The PSD of the jet-milled active pharmaceutical ingredient was characterized by a D10 of 7.8 μm, a D50 of 16.1 μm, and a D90 of 21.5 μm.

The specific surface area distributions of as-crystallized active pharmaceutical ingredient and jet-milled active pharmaceutical ingredient was determined by laser diffraction. The as-crystallized active pharmaceutical ingredient had a specific surface area of 291 m²/kg, and the jet-milled active pharmaceutical ingredient had a specific surface area of 478 m²/kg. In other samples, the jet milled active pharmaceutical ingredient was characterized by a specific surface area of 1174 m²/kg.

Certain properties of the active pharmaceutical ingredient used in Example 13 are provided in Table 3.

TABLE 3

Active pharmaceutical ingredient properties.

| Property | Units | As-Crystallized | Jet-Milled |
|---|---|---|---|
| API Bulk Density | g/mL | 0.20 | 0.12 |
| API Tapped Bulk Density | g/mL | 0.38 | 0.20 |
| Hausner Ratio | — | 1.85 | 1.700 |
| PSD (D10) | μm | 12 | 8 |
| PSD (D50) | μm | 34 | 16 |
| PSD (D90) | μm | 71 | 28 |
| Specific Surface Area | (m²/kg) | 291 | 478 |

Example 11

Friability Measurement

Granules between 200 μm to 350 μm were separated using 45-mesh and 70-mesh screens. The screened granulation was placed on a 200-mesh screen in a sonic sifter and then exposed to a very high vibration amplitude of 8 corresponding to 3,600 sonic energy pulses per minute for 2 minutes. The granulation was weighed before and after exposure to sonic vibration. About 1.02 wt % of the material passed through the 200-mesh screen. This material is considered to be fines that were caused by the attrition of the granules and defined as the friability.

Example 12

Pharmaceutical Granulation (12)

A granulation composition (800.0 g) was prepared by combining 98.5 wt % active pharmaceutical ingredient (394.0 g), 0.5 wt % binder 2.0 g), and 1.0 wt % antistatic agent (4.0 g), where wt % was based on the total weight of the mixture. The active pharmaceutical ingredient was the compound of Formula (2a), 4-((L-valyl)oxy)butanoic acid, and was jet-milled. The binder was Klucel® EXF HPC (hydroxypropylcellulose) (Ashland). The antistatic agent was Aerosil® 200 (hydrophilic fumed silica, BWT SA 200 m2/g) (Evonik Industries). Milling was done using a Comil® (Quadro Engineering).

The active pharmaceutical ingredient was milled with a 32R screen, with a square impeller and a 0.175-inch spacer and 1349.8 rpm.

The composition was separated into two, 400 g batches for granulation. Each sub-batch was granulated for about 6.75 minutes, with 12.1 g added water at a flow rate of about 1.8 g/min using an atomizing air pressure of 3.0 psi. The bed height was 4.0 cm. The mixer speed was 850 rpm and the chopper speed was 3600 rpm.

The two sub-batches were combined for wet massing.

The composition was wet massed for 10 minutes at a final temperature of 24.7° C. with a bed height of 8.0 cm and a mixer speed of 547 rpm and a chopper speed of 1800 rpm.

After wet massing, the composition was wet milled using a screen size of 32R, a square impeller and a 0.175-inch spacer at a speed if 3000 rpm.

The wet milled composition was then granulated for 22 min with 41 g (10.25 wt %) added water at a flow rate of 1.8 g/min and an atomizing air pressure of 3 psi. The bed height was 6.0 cm. The mixer speed was 850 rpm and the chopper speed was 3600 rpm.

The granulated composition was wet massed for 40 minutes at a temperature of from 24.7° C. to 30.9° C. with a final bed height of 5.2 cm and a mixer speed of 547 rpm and a chopper speed of 1800 rpm.

The granules were oven dried at 40° C. for 20 hours.

The dried granules had a bulk density of 0.41 g/mL, a Hausner Ratio of 1.38, and a surface area of 1174 m²/kg.

Example 13

Pharmaceutical Granulation (13)

A formulation (400.0 g) was prepared by combining 98.5 wt % active pharmaceutical ingredient (394.0 g), 0.5 wt % binder 2.0 g), and 1.0 wt % antistatic agent (4.0 g), where wt % was based on the total weight of the formulation. The active pharmaceutical ingredient was the compound of Formula (2a), 4-((L-valyl)oxy)butanoic acid and was jet-milled. The binder was Klucel® EXF HPC (hydroxypropylcellulose) (Ashland). The antistatic agent was Aerosil® 200 (hydrophilic fumed silica, BWT SA 200 m²/g) (Evonik Industries). Milling was done using a Comil® (Quadro Engineering).

The formulation was granulated using a GMX Granumeist® high shear granulator (Freund-Vector Corporation) with a 4 L jacketed bowl fitted with an impeller and a chopper.

The dry formulation was divided into two, 400 g sub-batches for wet granulation.

In a first wet granulation step, a total of 9.0 wt % (18.1 g) water was added during wet granulation, where wt % is with respect to the total weight of the dry formulation sub-batch. Water was added by dripping into the mixing bowl at a flow rate of about 2.0 g/min. The wet granulation was granulated for about 9.3 minutes at a mixer speed of 850 rpm and a chopper speed of 3,600 rpm, with an average temperature of the wet granulation of about 25° C. The bed height decreased by about 40% from 7.0 cm to 4.0 cm).

In a first wet massing step, the wet granulated sub-batches were combined and wet massed for 20 minutes at a mixer speed of 850 rpm and a chopper speed of 3,600 rpm, with an average temperature of the wet granulation from 20.0° C. to 23.4° C. The bed height decreased by about 30% from 7.0 cm to 5.0 cm.

In a second granulation step, the product of the first wet massing step was granulated for 26.7 minutes at a mixer speed of 850 rpm and a chopper speed of 3,600 rpm, with an average temperature of the wet granulation of 25.2° C. Water (53.6 g) was added by spraying using an atomizing air pressure of 4.0 psi at a distance of 4.19 cm from the granulation bed. The bed height deceased from 5.0 cm to 4.0 cm.

In a second wet massing step, the second wet granulation was wet massed for 40 minutes at a mixer speed of 850 rpm and a chopper speed of 3,600 rpm, with a temperature of the wet granulation of about 30° C. to 40° C. The bed height decreased by about 12% from 4.0 cm to 3.5 cm.

In a third granulation step, the product of the second wet massing step was granulated for 8.4 minutes at a mixer speed of 850 rpm and a chopper speed of 3,600 rpm, with an average temperature of the wet granulation of 25.2° C. Water (17.3 g) was added by spraying using an atomizing air pressure of 4.0 psi at a distance of 5.69 cm from the granulation bed. The bed height remained the same at about 3.5 cm.

In a third wet massing step, the third wet granulation was wet massed for 20 minutes at a mixer speed of 850 rpm and a chopper speed of 3,600 rpm, with a temperature of the wet granulation of about 30° C. to 40° C. The bed height decreased by about 14% from 3.5 cm to 3.0 cm.

In a fourth granulation step, the product of the third wet massing step was granulated for 8.3 minutes at a mixer speed of 850 rpm and a chopper speed of 3,600 rpm, with an average temperature of the wet granulation of 25.2° C. Water (17.3 g) was added by spraying using an atomizing air pressure of 4.0 psi at a distance of 5.9 cm from the granulation bed. The bed height decreased from 3.0 cm to 2.8 cm.

In a fourth wet massing step, the third wet granulation was wet massed for 20 minutes at a mixer speed of 850 rpm and a chopper speed of 3,600 rpm, with a temperature of the wet granulation of about 19° C. to 20° C. The bed height remained about the same at 3.0 cm.

The product of the fourth wet massing step was then wet milled using a Comil® fitted with a 032R screen at a milling speed of 3005 rpm using a square impeller, a 0.150-inch spacer.

In a fifth wet massing step, the wet milled granulation was wet massed for 20 minutes at a mixer speed of 850 rpm and a chopper speed of 3,600 rpm, with a temperature of the wet granulation of from 15° C. to 25° C. The bed height decreased from 3.0 cm to 2.4 cm.

The product of the fifth wet massing step was dried for 19 hours at 40° C.

A summary of the processing conditions used to prepare pharmaceutical granulation (13) is provided in Table 4.

TABLE 4

Processing conditions.

| | Granulation Conditions | | | | | | Wet Massing Conditions | | | |
| --- | --- | --- | --- | --- | --- | --- | --- | --- | --- | --- |
| Step | Time (min) | Water (g) | Flow Rate (g/min) | Atomizing Air (psi) | Start Bed Height (cm) | Ending Bed Height (cm) | Time (min) | Start Bed Height (cm) | Ending Bed Height (cm) | Temp. (° C.) |
| First Granulation Sub-Batch 1 | 9.4 | 18.1 | 1.9 | N/A | 7.0 | 4.0 | | | | |
| First Granulation Sub-Batch 2 | 9.2 | 18.2 | 2.0 | N/A | 7.0 | 4.0 | | | | |
| First Wet Massing | | | | | | | 20.0 | 7.0 | 5.0 | 20-25 |
| Second Granulation | 26.7 | 53.6 | 1.9-2.1 | 4.0 | 5.0 | 4.0 | | | | |
| Second Wet Massing | | | | | | | 40.0 | 4.0 | 3.5 | 30-40 |
| Third Granulation | 8.4 | 17.3 | 2.1 | 4.0 | 3.5 | 3.5 | | | | |
| Third Wet Massing | | | | | | | 20.0 | 3.5 | 3.0 | 35-37 |
| Fourth Granulation | 8.3 | 17.3 | 2.1 | 4.0 | 3.0 | 2.8 | | | | |
| Fourth Wet Massing | | | | | | | 20.0 | 3.0 | 3.0 | 19-20 |
| [1] Wet Milling | | | | | | | | | | |
| Fifth Wet Massing | — | — | — | — | — | — | 20 | 3.0 | 2.4 | 18-24 |

[1] Wet milling with a 0.32R screen, a milling speed of 3005, and using a square impeller and a 0.150 spacer.

About 35% of the granules had a particle size greater than 500 µm, 53% had a particle size from 210 µm to 500 µm, and 28% had a particle size less than 210 µm, where particle size was determined by sieve analysis.

Certain properties of pharmaceutical granulation (13) are shown in Table 5

TABLE 5

Pharmaceutical granulation (13) properties.

| Property | Units | Example 13 |
| --- | --- | --- |
| API Bulk Density | g/mL | 0.12 Jet Milled |
| Bulk Density | g/mL | 0.638 |
| 135-70 mesh Bulk density | g/mL | 0.600 |
| [1] 35-70 mesh Batch Yield | % | 53 |

TABLE 5-continued

Pharmaceutical granulation (13) properties.

| Property | Units | Example 13 |
|---|---|---|
| [2] >35 mesh Batch Yield | % | 19 |
| [3] <70 mesh Batch Yield | % | 28 |

[1] 212 μm to 500 μm.
[2] >212 μm.
[3] <500 μm.

FIGS. 19 and 20 show photographs of the granules at 100× and 240× magnification, respectively.

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. Granules comprising:
greater than 95 wt % of a compound of Formula (2a):

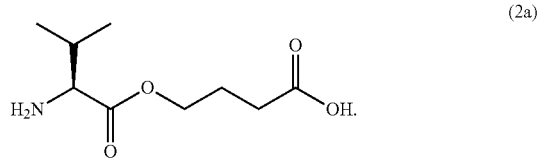

(2a)

or a pharmaceutically acceptable salt thereof, wherein the compound of Formula (2a) has an aqueous solubility greater than 100 mg/mL;
from 0.1 wt % to 1.0 wt % of a binder; and
from 0.1 wt % to 2.0 wt % of an antistatic agent;
wherein wt % is based on the total weight of the granules; and
wherein the granules are characterized by:
a particle size distribution (PSD) D10 from 50 μm to 150 μm, a D50 from 150 μm to 350 μm, and a D90 from 475 μm to 725 μm, wherein the particle size distribution is determined by laser diffraction or by sieve analysis;
a loss on drying (LOD) from 0.05 wt % to 1.5 wt %, wherein wt % is based on the weight of the granules after drying;
a friability value less than 2 wt %, wherein friability is determined using a sonic sifter; and
a bulk density from 0.50 g/mL to 1.20 g/mL, wherein bulk density is determined according to USP 616, Method I.

2. The granules of claim 1, wherein the compound of Formula (2a) is characterized by a particle size distribution characterized by a D10 from 1 μm to 3 μm, a D50 from 6.5 μm to 8.5 μm, and a D90 from 15 μm to 17 μm, wherein the particle size distribution is determined by laser diffraction or by sieve analysis.

3. The granules of claim 1, wherein the compound of Formula (2a) has a specific surface area from 200 m$^2$/kg to 1200 m$^2$/kg, wherein the specific surface area is determined by laser diffraction.

4. The granules of claim 1, wherein the compound of Formula (2a) is characterized by a bulk density from 0.1 g/mL to 0.4 g/mL, wherein the bulk density is determined according to USP 616, Method 1.

5. The granules of claim 1, wherein the granules comprise from 96 wt % to 99.5 wt % of the compound of Formula (2a), wherein wt % is based on the total weight of the granules.

6. The granules of claim 1, wherein the granules are characterized by a friability less than 1.10 wt %, wherein wt % is based on the total weight of the granules, and the friability is determined using a sonic shifter.

7. The granules of claim 1, wherein the granules comprise:
from 98 wt % to 99 wt % of the compound of Formula (2a);
from 0.25 wt % to 0.75 wt % of the binder; and
from 0.5 wt % to 1.5 wt % of the antistatic agent,
wherein wt % is based on the total weight of the granules.

8. The granules of claim 1, wherein the granules consist of:
from 98 wt % to 99 wt % of the compound of Formula (2a);
from 0.25 wt % to 0.75 wt % of the binder; and
from 0.5 wt % to 1.5 wt % of the antistatic agent,
wherein wt % is based on the total weight of the granules.

9. The granules of claim 1, wherein the binder comprises hydroxypropyl cellulose.

10. The granules of claim 1, wherein the antistatic agent comprises hydrophilic fumed silica.

11. The granules of claim 1, wherein the granules comprise a coating.

12. A pharmaceutical composition comprising the granules of claim 1.

13. The pharmaceutical composition of claim 12, wherein the pharmaceutical composition comprises an oral suspension.

14. The pharmaceutical composition of claim 12, wherein the pharmaceutical composition comprises an immediate release formulation.

15. The pharmaceutical composition of claim 12, wherein the pharmaceutical composition comprises a controlled release formulation.

16. The granules of claim 1, wherein the granules comprise a controlled release coating.

17. The granules of claim 1, wherein,
the binder comprises hydroxypropyl cellulose; and
the antistatic agent comprises hydrophilic fumed silica.

18. The granules of claim 1, wherein the granules are characterized by an average sphericity greater than 0.90, wherein sphericity is determined using wet dispersion particle shape methods or by dynamic image analysis.

* * * * *